(12) United States Patent
Bailey et al.

(10) Patent No.: US 10,695,193 B2
(45) Date of Patent: Jun. 30, 2020

(54) DEVICE AND METHOD FOR INSERTING A LINER INTO AN ACETABULAR CUP

(71) Applicant: DEPUY IRELAND UNLIMITED COMPANY, County Cork (IE)

(72) Inventors: Andrew Bailey, Leeds (GB); Gary Moore, Wetherby (GB)

(73) Assignee: DEPUY IRELAND UNLIMITED COMPANY (IE)

( * ) Notice: Subject to any disclaimer, the term of this patent is extended or adjusted under 35 U.S.C. 154(b) by 40 days.

(21) Appl. No.: 15/569,023

(22) PCT Filed: Apr. 27, 2016

(86) PCT No.: PCT/EP2016/059371
§ 371 (c)(1),
(2) Date: Oct. 24, 2017

(87) PCT Pub. No.: WO2016/174067
PCT Pub. Date: Nov. 3, 2016

(65) Prior Publication Data
US 2018/0125664 A1    May 10, 2018

(30) Foreign Application Priority Data
Apr. 28, 2015 (GB) .................................. 1507211.9

(51) Int. Cl.
*A61F 2/46* (2006.01)
*A61F 2/34* (2006.01)
*A61F 2/30* (2006.01)

(52) U.S. Cl.
CPC .............. *A61F 2/4609* (2013.01); *A61F 2/34* (2013.01); *A61F 2/4637* (2013.01); *A61F 2002/305* (2013.01); *A61F 2002/30331* (2013.01); *A61F 2002/30716* (2013.01)

(58) Field of Classification Search
CPC ......... A61F 2/34; A61F 2/4609; A61F 2/4637
See application file for complete search history.

(56) References Cited

U.S. PATENT DOCUMENTS

| 5,472,415 | A | | 12/1995 | King et al. | |
|---|---|---|---|---|---|
| 6,063,123 | A | * | 5/2000 | Burrows | ................... A61F 2/34 606/86 R |
| 6,468,281 | B1 | * | 10/2002 | Badorf | .................. A61F 2/4637 606/91 |
| 6,589,284 | B1 | | 7/2003 | Silberer | |

(Continued)

FOREIGN PATENT DOCUMENTS

| CN | 102481193 A | 5/2012 |
|---|---|---|
| CN | 103096842 A | 5/2013 |

(Continued)

*Primary Examiner* — Christian A Sevilla

(57) ABSTRACT

A device and method for inserting a liner into an acetabular cup. The device includes a first portion configured to engage the liner and a rim of the acetabular cup to align a pole of the liner and a pole of the cup along an axis of the device prior to insertion of the liner into the cup. The device also includes a second portion for pushing the liner into the cup. The second portion includes a guide arrangement for engaging a rim of the liner. The second portion is coupled to the first portion for movement of the second portion with respect to the first portion along said axis.

24 Claims, 14 Drawing Sheets

(56) References Cited

U.S. PATENT DOCUMENTS

| | | | |
|---|---|---|---|
| 2005/0149043 A1* | 7/2005 | Parry | A61F 2/4609 606/91 |
| 2007/0219562 A1 | 9/2007 | Slone et al. | |
| 2007/0219640 A1 | 9/2007 | Steinberg | |

FOREIGN PATENT DOCUMENTS

| | | |
|---|---|---|
| EP | 972499 A2 | 1/2000 |
| EP | 2898860 A1 | 7/2015 |
| JP | 2012511982 A | 5/2012 |
| WO | WO 2004069107 A1 | 8/2004 |
| WO | WO 2008106598 A1 | 9/2008 |
| WO | WO 2011161166 A1 | 12/2011 |

* cited by examiner

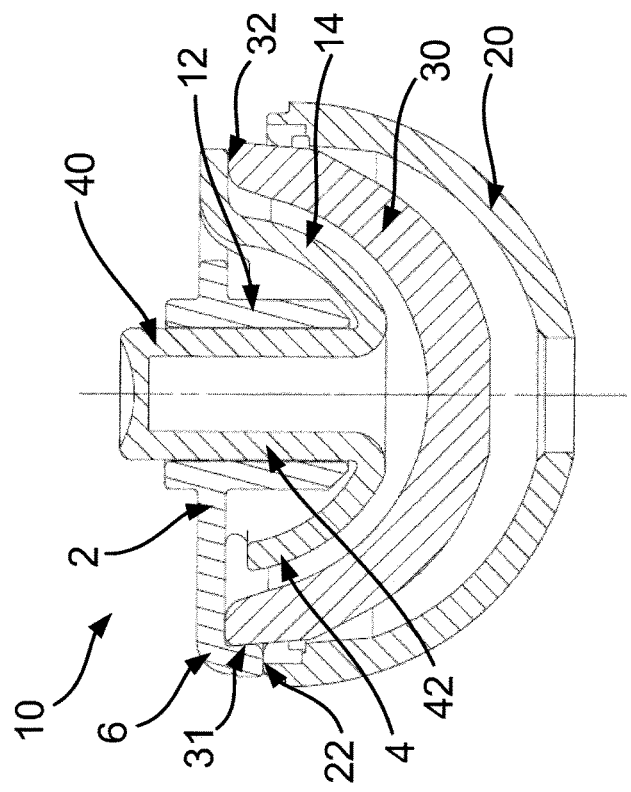
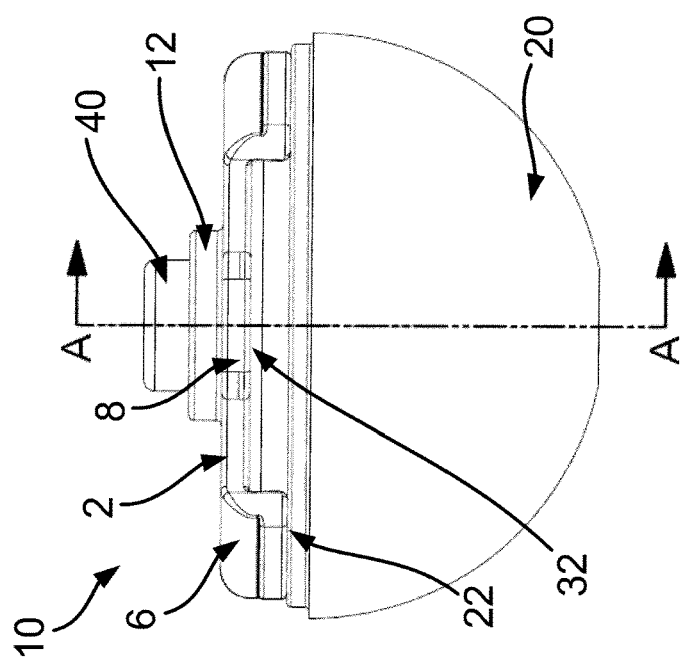
Fig. 3B
Fig. 3A

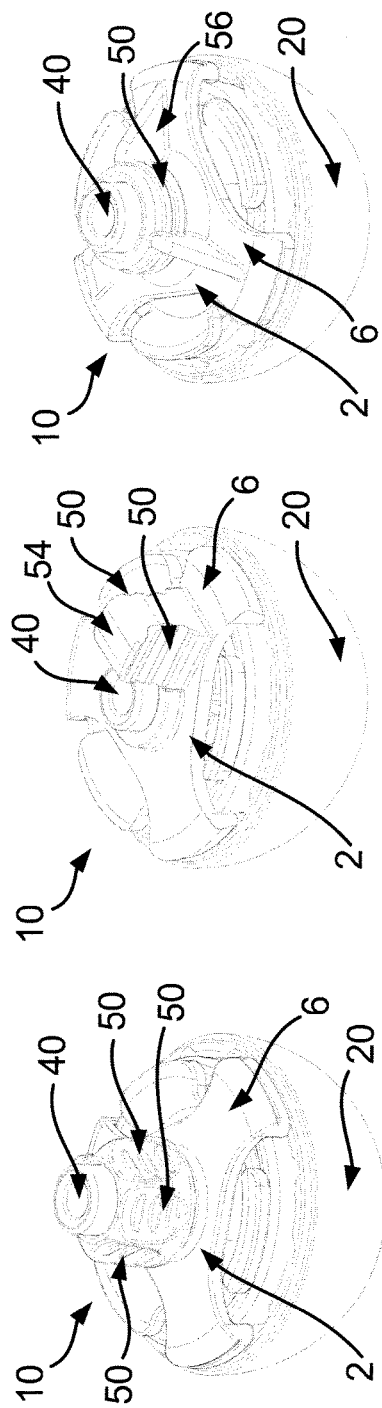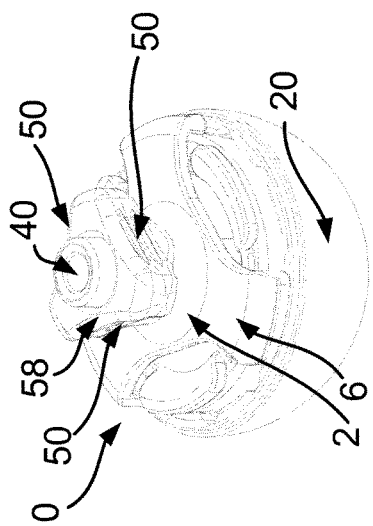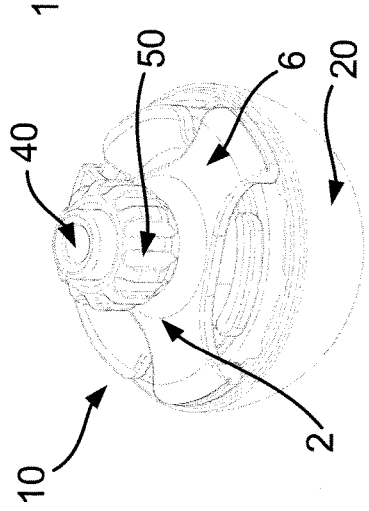

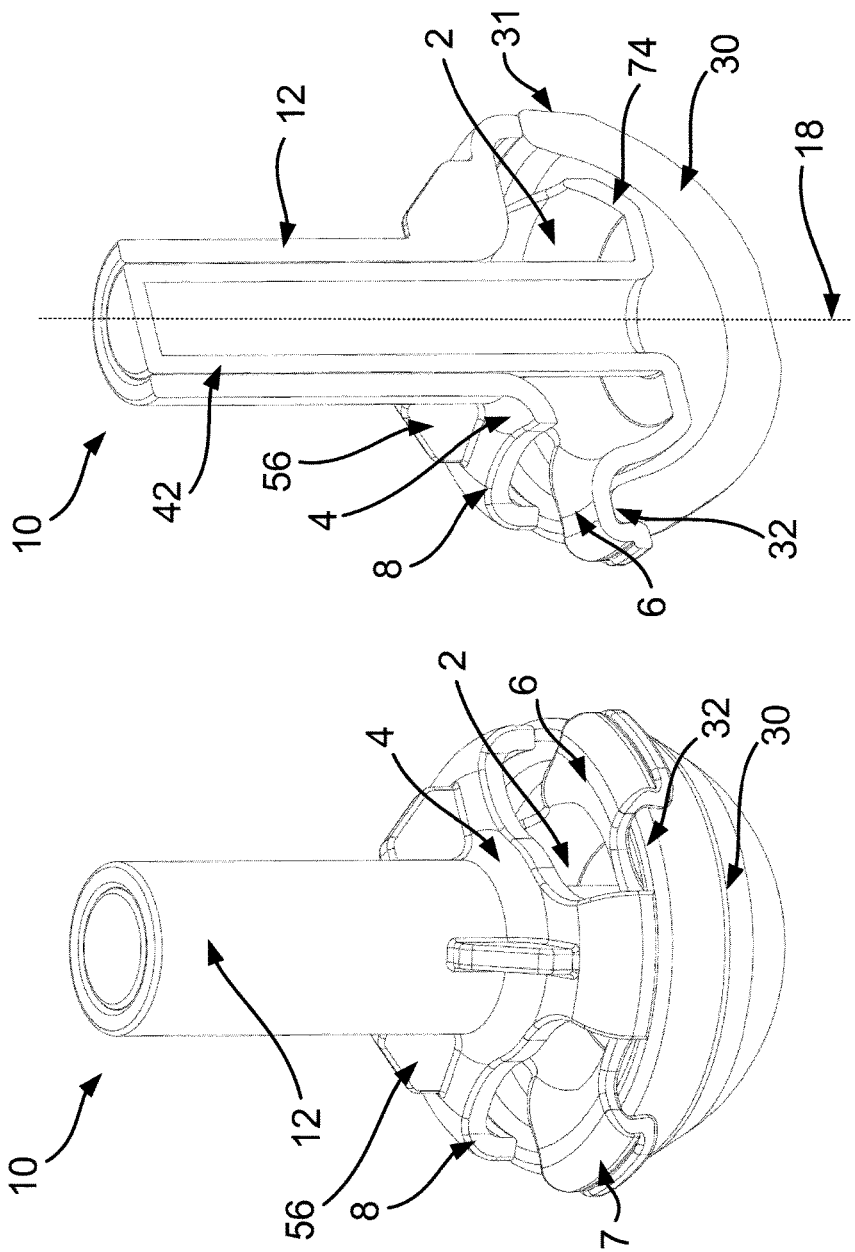

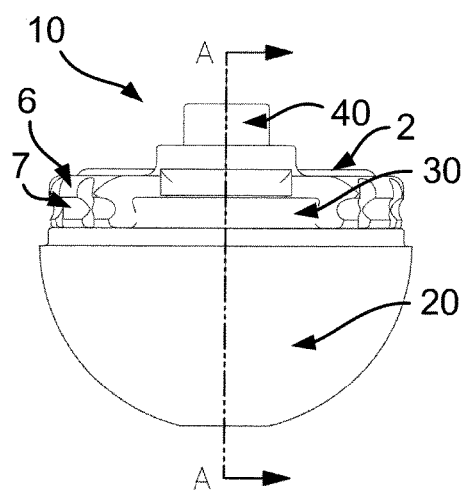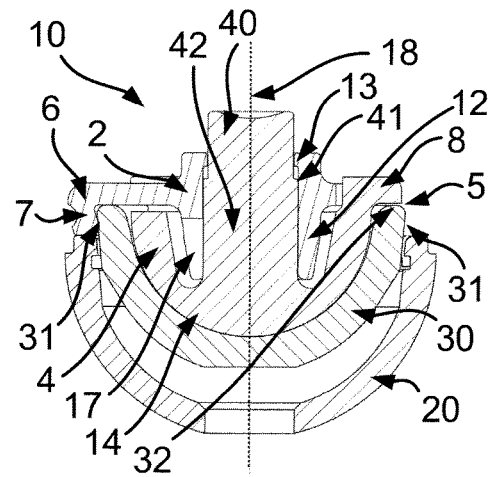
Fig. 11A  Fig. 11B
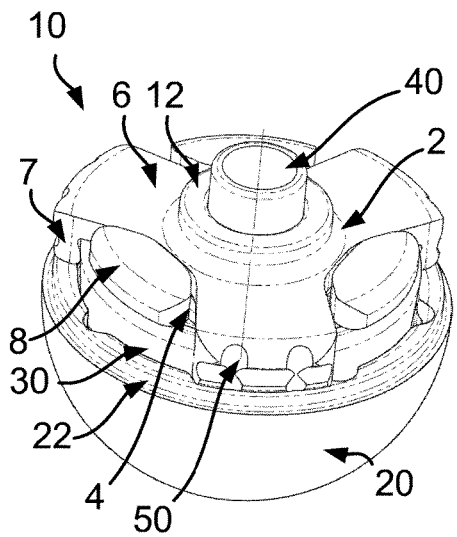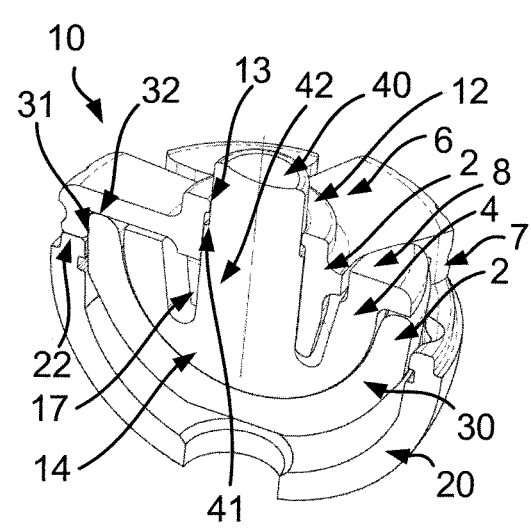
Fig. 12A  Fig. 12B

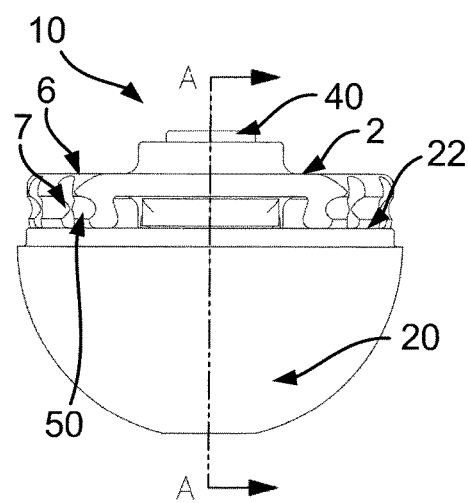
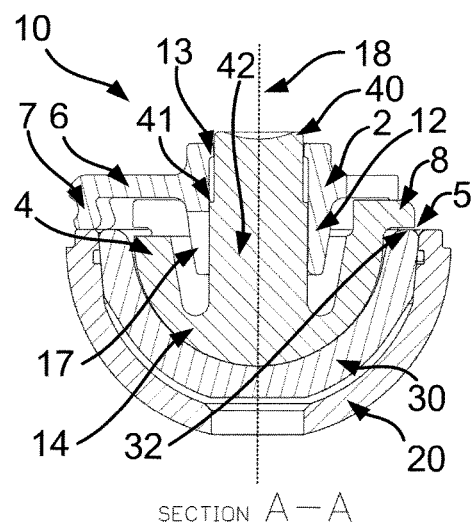
Fig. 13A  Fig. 13B
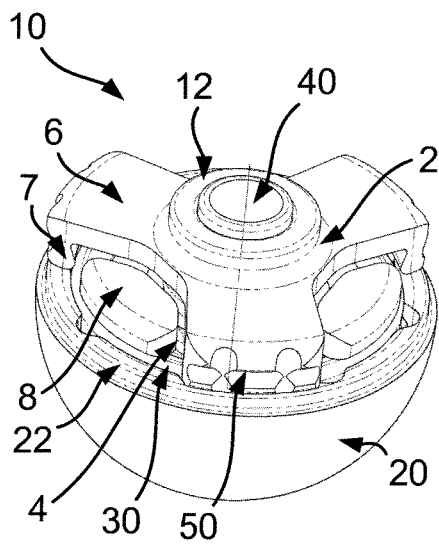
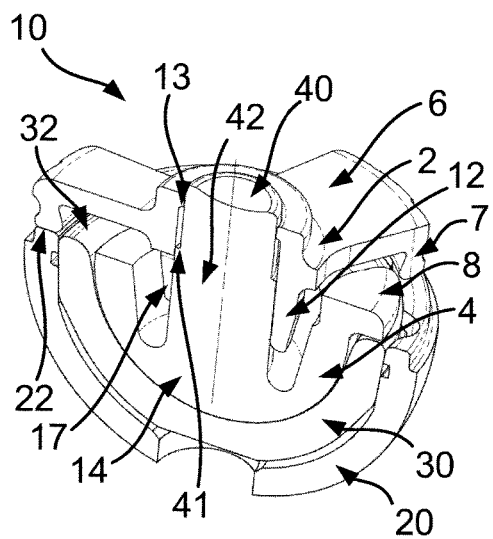
Fig. 14A  Fig. 14B

DEVICE AND METHOD FOR INSERTING A LINER INTO AN ACETABULAR CUP

CROSS REFERENCE TO RELATED APPLICATION

This application is a National Stage 35 U.S.C. 371 of International Patent Application PCT/EP2016/059371 filed Apr. 27, 2016, which claims priority to United Kingdom Application No. 1507211.9, filed Apr. 28, 2015, which are both incorporated by reference in their entireties.

FIELD OF THE INVENTION

This invention relates to a device and method for inserting a liner into an acetabular cup.

BACKGROUND OF THE INVENTION

A hip joint prosthesis includes an acetabular component and a femoral component. The acetabular component often includes a shell (or maybe cup) part, which is implanted in the patient's acetabulum, and a liner. The femoral component includes a stem part which fits into the intramedullary canal of the patient's femur. The stem part has a neck at its proximal end. A head part is fitted on to the neck. The convex surface of the head part provides a femoral component bearing surface which acts against the corresponding bearing surface in the acetabular component provided by concave internal surface of the liner.

The liner can allow smooth movement of the head part within the acetabular cup. During surgery, the liner is inserted into the cup after the cup has been installed in the acetabulum of the patient. It is important that when the liner is inserted into the cup, the liner is aligned correctly with respect to the cup. The cup and the liner are usually substantially hemispherical. For correct alignment, it is generally required that the pole of the substantially hemispherical liner coincides with the pole of the substantially hemispherical cup. In this configuration, the rims of the cup and the liner are generally also in alignment (e.g. contained within a common plane).

Misalignment of the liner with respect to the acetabular cup can lead to a number of problems. If the misalignment is noticed during surgery, the surgical procedure may need to be extended to correct the problem. If the misalignment is not noticed, it can lead to restricted movement of the hip joint, component loosening, component damage (e.g. cracking) and potentially the need for further surgery to correct the problem.

Devices are available that assist in inserting the liner into the acetabular cup. These devices are typically mounted on the liner itself prior to positioning the liner over the cup for insertion. Some devices of this kind allow for initial alignment of the liner with respect to the cup prior to insertion. However, these devices are prone to tilting of the liner as it is inserted into the cup, leading to misalignment.

WO 2011/161166 describes an insertion instrument for instrumented insertion of a socket inset with a spherical cap into a hip socket of a hip-joint prosthesis, having an impacting instrument with a handle, at one end of which a holding tool for the socket inset is located.

WO 2008/106598 describes an acetabular liner insertion guide that aligns a liner within an acetabular shell. The liner includes a ring and a penetrable layer. The ring includes a lip configured to rest on an upper surface of the acetabular shell. The ring is also configured to attach to the liner such that an upper surface of the liner is in a plane that is generally parallel to a plane that includes the upper surface of the acetabular shell. The penetrable layer is configured to receive an impactor and overlie the liner. When the insertion guide is placed on the shell and the impactor impacts the liner, the insertion guide separates from the liner and remains on the impactor.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a device for inserting a liner into an acetabular cup. The device includes a first portion configured to engage the liner and a rim of the acetabular cup to align a pole of the liner and a pole of the cup along an axis of the device prior to insertion of the liner into the cup. The device also includes a second portion for pushing the liner into the cup. The second portion includes a guide arrangement for engaging a rim of the liner. The second portion is coupled to the first portion for movement of the second portion with respect to the first portion along said axis.

According to another aspect of the invention, there is provided a method for inserting a liner into an acetabular cup. The method includes engaging a first portion of an insertion device with the liner and a rim of the acetabular cup to align a pole of the liner and a pole of the cup along an axis of the device prior to insertion of the liner into the cup. The method also includes using a second portion of the insertion device to push the liner along the axis into the cup. The second portion includes a guide arrangement for engaging a rim of the liner. The second portion is coupled to the first portion for linear movement of the second portion with respect to the first portion along the axis.

Embodiments of this invention can allow a liner to be inserted into an acetabular cup in a manner that can ensure that the liner is correctly aligned with the cup. The first portion of the device can be used to allow initial alignment of the liner with respect to the cup, prior to inserting the liner. This may be achieved by engaging a first portion of an insertion device with the liner and with a rim of the cup to align a pole of the liner and a pole of the cup along an axis of the device. The second portion of the device can then be used to push the liner along the axis of the device into the cup, so that the poles of the liner and the cup meet each other as the liner is inserted. The guide arrangement of the second portion of the device can act to guide the liner as it is inserted, for example to prevent tilting of the liner with respect to the axis of the device. The coupling between the first portion and the second portion allows linear movement of the second portion along the axis of the device, so that a force applied to the second portion for pushing the liner into the cup causes the liner to move along the axis of the device, even if the force applied to the second portion is slightly off-axis.

It has been found that embodiments of this invention consistently allow a liner to be correctly inserted into an acetabular cup without misalignment of the liner. Correct insertion of the liner has even been found to be consistently achievable when the user of the device is not able to view the device while operating it.

The first portion can provide a stable base for positioning the device on the cup to initially align the pole of the cup with the device axis and to keep the device aligned with the cup as the liner is inserted. In some embodiments, the first portion can include at least three arms for engaging the liner and a rim of the acetabular cup at spaced apart points around the liner and the rim of the cup. The provision of at least three equally spaced arms can ensure that the base provided by the first portion does not tilt during use of the device. In some examples, the first portion can include more than three arms.

In some embodiments, the guide arrangement may include a plurality of guide members for engaging the rim of the liner at spaced apart points around the rim. In some embodiments the guide arrangement may include at least three guide members.

In some embodiments, in an initial position of the device prior to insertion of the liner into the cup, a gap may be present between the guide members of the guide arrangement and the rim of the liner. The guide members may be positioned to engage with the rim of the liner for preventing tilting of the liner as the liner is pushed into the cup. The size of the gap may be relatively small, so that only a minimal amount of tilting of the liner may take place before one or more of the guide members engages with the rim of the liner to prevent further tilting. It is also envisaged that in some embodiments the guide members may engage with the rim of the liner in the initial positon prior to the insertion of the liner into the cup (e.g. in embodiments in which the guide members are configured to apply some or all of the force for pushing the liner into the cup.

The guide members of the second portion may, in some embodiments, engage the rim of the liner at equally spaced points around the rim. This arrangement can allow the forces applied to the rim of the liner by the second portion to be balanced around the device axis, which may further reduce any tendency of the liner to tilt with respect to the device axis as it is inserted into the cup. For similar reasons, the arms of the first portion can engage the liner and the rim of the acetabular cup at equally spaced points around the liner and the rim of the cup.

In some embodiments, the positions of the arms of first portion and the guide members of the second portion may be adjustable for varying a lateral distance of the arms and the guide members from the axis of the device according to the size of the cup and the liner. This can allow the device to be used with acetabular cups and liners of different sizes. The arms of the first portion and the guide members of the second portion may extend at an acute angle with respect to the axis of the device. The device may further include an outer sleeve that is configured to adjust the positions of the arms and guide members by sliding along the device in a direction parallel to the axis to push the arms and guide members inward toward the axis. This arrangement can allow you convenient adjustment of the arms of the first portion and the guide members of the second portion to match them to the size of the cup and liner.

The first portion may be configured to grip an outer surface of the liner adjacent a rim of the liner. This can allow a surgeon to first engage the first portion with the liner before positioning the liner over the acetabular cup without needing to hold into the liner. This can simplify the process of aligning the pole of the liner and the pole of the cup along the axis of the device prior to insertion of the liner into the cup.

In some embodiments, a guide sleeve with a rod slidably received therein can be used for coupling the first portion and the second portion. This arrangement can ensure linear movement of the second portion with respect to the first portion along the axis. Either the first portion can include the guide sleeve and the second portion can include the rod, or vice versa.

An inner surface of the guide sleeve may include a lip located toward a distal end of the guide sleeve. The lip may extend inwardly towards the device axis for forming an interference fit with the rod. This can prevent inadvertent separation of the first portion and the second portion during a surgical procedure. The lip may be located at a distal end of the sleeve. The distal end of the guide sleeve may also include a plurality of slots extending substantially parallel to the device axis. The slots may divide the distal end of the guide sleeve into a plurality of arms which extend substantially parallel to the device axis. These arms can provide a degree of resilience for the engagement of the lip with an outer surface of the rod, to form the interference fit. The lip may be divided by the slots into a plurality of parts, each part being located on (e.g. at a distal tip of) a respective one of the arms.

In one embodiment, an outer surface of the rod may include a ridge and an inner surface of the guide sleeve may include a lip, which is located at a proximal end opening of the guide sleeve. The lip and the ridge may be configured to prevent inadvertent reverse mounting of the first portion and the second portion.

The second portion can include a button for manually pushing the second portion along the axis of the device. This can allow a surgeon to insert the liner into the cup simply by pushing the button of the second portion with a finger or thumb. In an alternative approach, the second portion can include connection means for connecting the second portion to a tool for applying a force to the second portion to push the second portion along the axis of the device.

The first portion and/or the second portion can include one or more gripping surfaces for manually gripping the device while the liner is inserted. The gripping surfaces can allow a surgeon to hold the device steady while the liner is inserted.

The guide members of the guide arrangement of the second portion may be configured to push the liner into the cup as the second portion moves relative to the first portion. Thus, the guide members in some embodiments can apply the force for inserting the liner while also acting as guides to prevent tilting of the liner.

The second portion can include an engagement member for engaging an inner surface of the liner at the pole of the liner for pushing the liner into the cup as the second portion moves relative to the first portion. The engagement member may have a substantially hemispherical curved outer surface for engaging with the inner surface of the liner. The guide members of the guide arrangement of the second portion can engage the rim of the liner to prevent tilting of the liner relative to the axis of the device. In this embodiment, the force for inserting the liner is applied to the liner at its pole by the engagement member, while the guide members of the guide arrangement can act to prevent tilting of the device during insertion of the liner. In this embodiment, there may be a gap between the guide members and the rim of the liner in initial position of the device prior to insertion of the liner, as noted above.

The various features of the device, such as the first portion and the second portion can be formed from a polymer. The polymer used can be rigid enough to withstand the forces applied to the components of the device during use, and can have a melting point high enough to allow the device to be sterilised before use. The polymer may be an acetal, a nylon, a sulfone polymer or any other suitable kind of polymer. In one embodiment, the polymer may be Polyether ether ketone (PEEK). It is also envisaged that the materials used to manufacture the device may include radiopaque materials, to allow the device to be viewed in X-rays taken during a hip replacement procedure.

In one embodiment, there can be provided an apparatus including a liner and device for inserting the liner into an acetabular cup. The device includes a first portion that is engaged with the liner. The first portion can also engage a rim of the acetabular cup to align a pole of the liner and a pole of the cup along an axis of the device prior to insertion of the liner into the cup. The device also includes a second portion for pushing the liner into the cup. The second portion includes a guide arrangement that may have at least three guide members that are engaged with a rim of the liner at spaced apart points around the rim. The second portion is coupled to the first portion for linear movement of the second portion with respect to the first portion along the axis. The apparatus may further include the acetabular cup—in such embodiments, the first portion is engaged with the rim of the acetabular cup as noted above.

In some embodiments, the device may include features for preventing re-use after the liner has been inserted in the cup. These features may include one or more non-return members configured to block movement of the second portion with respect to the first portion after the liner has been inserted.

The non-return members may include, for instance, one or more flexible arms. The arms may be arranged, in an initial position of the device, prior to insertion of the liner into the cup, to urge against an outer surface of a guide sleeve of the device. As the second portion is moved with respect to the first portion, the flexible arms may slide along the outer surface of the guide sleeve. The flexible arms may move inward toward the axis of the device when the arms reach an end of the guide sleeve, to reach a final position in which they block movement of the second portion with respect to the first portion. This can prevent the device returning to the initial position.

A plurality of such flexible arms may be located at spaced apart points around the guide sleeve. The points may be regularly spaced.

In one embodiment, the device may include one or more apertures for receiving a tool to splay said flexible arms apart to receive the guide sleeve during assembly of the device.

In embodiments in which the device includes a guide sleeve with a rod slidably received therein for coupling the first portion and the second portion, the non-return members may include one or more collet fingers comprised in the guide sleeve. The rod may include an opening for receiving the collet fingers as the liner is inserted into the cup.

According to an aspect of the invention, there is provided a single use device for inserting a liner into an acetabular cup. The device has a first portion configured to engage the liner and a rim of the acetabular cup to align the liner and the acetabular cup with an insertion axis of the device prior to insertion of the liner into the acetabular cup. The device has also a second portion coupled to the first portion for pushing the liner into the acetabular cup. The device has also a non-return member for preventing reuse of the device. The device is moveable from an initial configuration to a deployed configuration. In the initial configuration, the non-return member is configured such that the second portion may be moved with respect to the first portion along the insertion axis in a first direction to seat the liner into the acetabular cup. In the deployed configuration, the non-return member transitions to a configuration in which movement along the insertion axis in a second direction, opposite to the first direction, is prevented. In this way, the device may be configured to prevent the device being returned to the initial configuration.

The non-return member may include, for instance, one or more resilient members. The resilient member or members may be resiliently biased towards a blocking arrangement in which they abut one of the first portion or the second portion and prevent movement in the second direction. In the initial configuration, the resilient member or members are held against the bias so that the second portion may be moved with respect to the first portion along the insertion axis. In the deployed configuration, the resilient member or members are in the blocking arrangement.

The first portion may have a guide sleeve in which a rod of the second portion is slidably positioned to couple the second portion to the first portion. The guide sleeve may define the insertion axis along which the second portion moves as the device transitions from the initial configuration to the deployed configuration. In the deployed configuration, the non-return member may be resiliently biased to abut one of the guide sleeve or the rod in order to prevent movement in the second direction.

In embodiments where the first portion has a guide sleeve in which a rod of the second portion is slidably received for coupling the first portion and the second portion, the non-return member may be provided on the first portion. The non-return member may include one or more collet fingers comprised in a guide sleeve that are biased towards a blocking arrangement. The rod may include a normal diameter section, a reduced diameter section and a shoulder at the transition between the normal and reduced diameter section. In the initial configuration, the collet fingers are splayed apart against the bias by the normal diameter section. In the deployed configuration, the collet fingers are in the blocking arrangement in which the collet fingers are located in the reduced diameter section in order to abut the shoulder and prevent movement in the second direction.

Alternatively, in embodiments where the first portion has a guide sleeve with a rod of the second portion slidably received therein for coupling the first portion and the second portion, the non-return member may be provided on the second portion. The non-return members may be resiliently biased towards a blocking configuration. In the initial configuration, the non-return member are held against the bias by and are slidable relative to the guide sleeve. In the deployed configuration, the non-return member is in the blocking configuration in which it abuts an end of the guide sleeve in order to prevent movement in the second direction. The non-return member may have one or more resilient arms located adjacent the rod. The resilient arm or arms may, in the initial configuration, be urged away from the rod against the bias by an outer surface of the guide sleeve. As the second portion is moved with respect to the first portion, the resilient arms may slide along the outer surface. The resilient arm or arms may move inward towards the rod when the resilient arm or arms reach an end of the guide sleeve, to reach the blocking configuration and block movement of the second portion with respect to the first portion thereby preventing the device returning to the initial configuration. When the non-return member comprises a plurality of resilient arms, they may be located at spaced apart points around the guide sleeve. The points may be regularly spaced. The device may include one or more apertures for receiving a tool to splay said non-return members apart to receive the guide sleeve during assembly of the device.

According to an aspect of the invention, there is provided a kit comprising a device of the kind described above and at least one liner. The kit may also include at least one acetabular cup. In one embodiment, the device can be provided in a kit that includes multiple liners and/or acetabular cups of various sizes.

BRIEF DESCRIPTION OF THE DRAWINGS

Embodiments of the present invention will be described hereinafter, by way of example only, with reference to the accompanying drawings in which like reference signs relate to like elements and in which:

FIG. 3A is a side view of the device of FIG. 1A;

FIG. 3B is a cross section along the line A-A in FIG. 3A;

FIGS. 4A-4E each show a device according to an embodiment of the invention, each embodiment including one or more gripping surfaces for holding the device during insertion of the liner;

FIG. 8A shows a device for inserting a liner into an acetabular cup in accordance with a further embodiment of the invention;

FIG. 8B is a cut-away view of the device of FIG. 8A;

FIG. 11A shows a device for inserting a liner into an acetabular cup in accordance with an embodiment of the invention;

FIG. 11B shows a cross section of the device of FIG. 11A;

FIG. 12A shows another view of the device of FIG. 11A;

FIG. 12B shows a cut-away view of the device of FIG. 11A;

FIG. 13A shows the device of FIG. 11A, after the liner has been inserted into the cup;

FIG. 13B shows a cross section of the device in FIG. 13A;

FIG. 14A shows another view of the device in FIG. 13A;

FIG. 14B shows a cut-away view of the device in FIG. 13A;

DETAILED DESCRIPTION

Embodiments of the present invention are described in the following with reference to the accompanying drawings.

Embodiments of this invention can provide a device for inserting a liner into an acetabular cup. The device can include a first portion and a second portion that are coupled together for linear movement of the second portion with respect to the first portion along an axis of the device. The linear movement of the second portion with respect to the first portion can, as will be explained in more detail below, act to prevent (or at least inhibit) tilting of the liner as it is inserted.

The first portion is configured to engage the liner and to engage a rim of the cup so that a pole of the liner (which may be substantially hemispherical in shape) and a pole of the acetabular cup (which may also be substantially hemispherical in shape) can be aligned along the above-mentioned device axis. The first portion can thus allow for initial alignment of the liner, the acetabular cup and the device such that the direction of movement of the second portion (and consequently the liner, as explained below) with respect to the first portion corresponds to an axis containing the poles of both the liner and the acetabular cup.

The second portion of the device is suitable for pushing the liner into the cup. The second portion has a guide arrangement for engaging a rim of the liner at spaced apart points around the rim. The guide arrangement can, in some embodiments, act to guide the liner as it is inserted into the cup. For instance the engagement of the guide arrangement with the rim of the liner can prevent tilting of the liner. Additionally, the guide arrangement can, in some embodiments, act to apply a force for the insertion of the liner, whereby the guide arrangement can act to push the liner into the cup as well as preventing tilting of the liner.

Accordingly, embodiments of this invention can allow for controlled insertion of a liner into an acetabular cup in a manner that can ensure the pole of the liner meets the pole of the cup, owing to: (i) the initial alignment of the poles of the liner and the cup along the device axis; followed by (ii) movement of the second portion along the device axis, and the action of the guide arrangement of the second portion to prevent tilting of the liner.

In some examples, the guide arrangement can include a number of guide members. For instance, the guide arrangement may include three or more guide members. The guide members of the guide arrangement may engage the rim of the liner at spaced apart points around the rim.

Figure 1A:
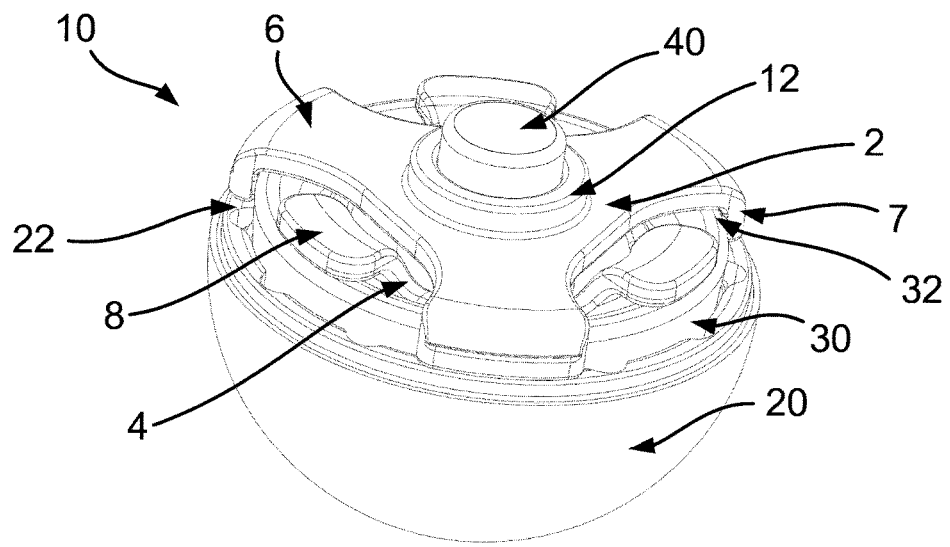
FIG. 1A shows a device for inserting a liner into an acetabular cup in accordance with an embodiment of the invention.
Figure 1B:
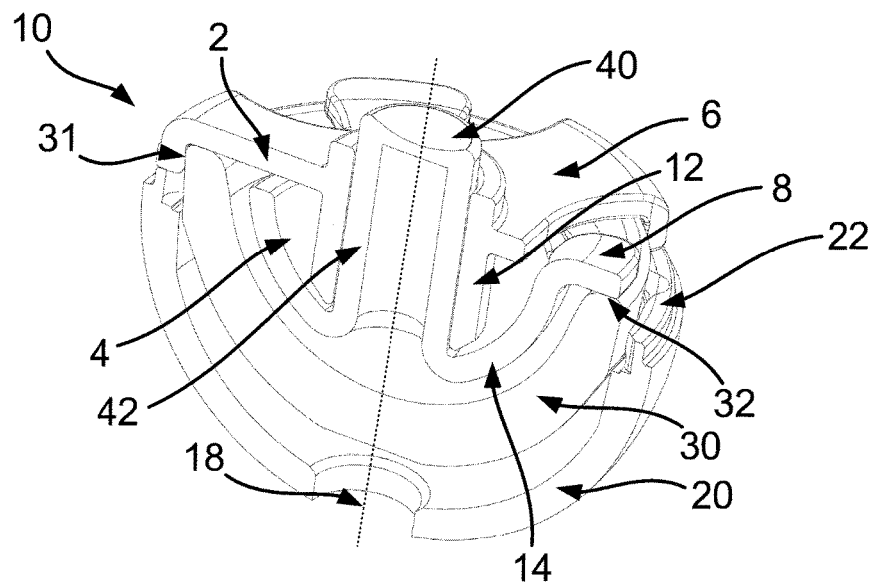
FIG. 1B is a cut-away view of the device of FIG. 1A.
Figure 2A:
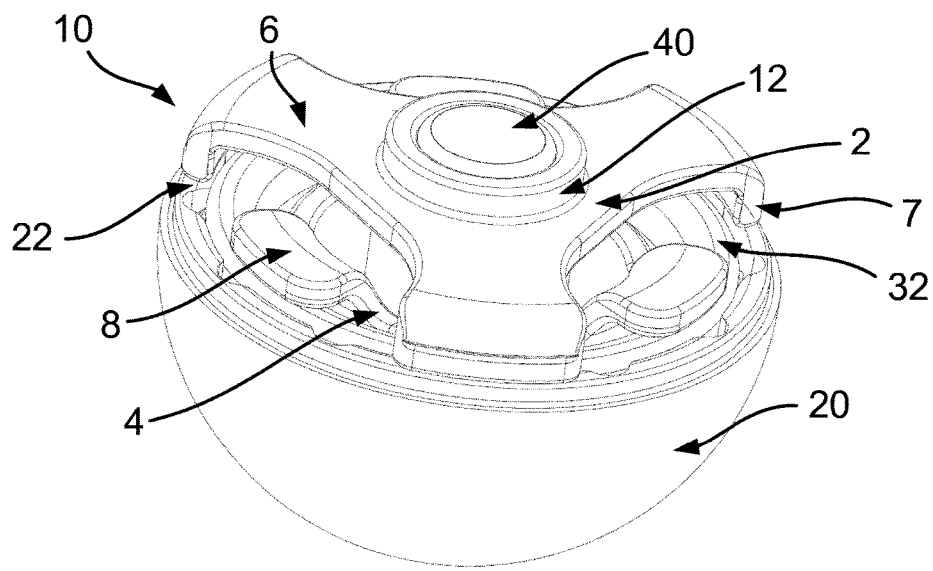
FIG. 2A shows the device of FIG. 1, after the liner has been inserted into the cup.
Figure 2B:
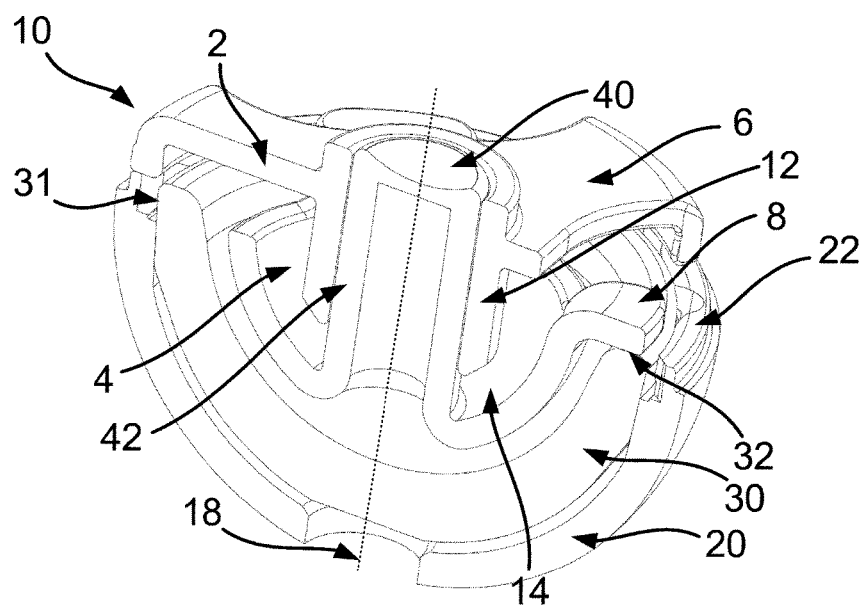
FIG. 2B is a cut-away view of the device in FIG. 2A.

FIGS. 1 to 3 show a device 10 for inserting a liner 30 into an acetabular cup 20 in accordance with the first embodiment of this invention. In particular, FIG. 1A shows the device 10 in an initial position, prior to insertion of the liner 30 into the acetabular cup 20, while FIG. 2A shows the device 10 after the liner 30 has been inserted into the cup 20. FIGS. 1B and 2B are cutaway views of the device 10, liner 30 and cup 20 corresponding to the positions shown in FIGS. 1A and 2A, respectively. FIG. 3A shows a side view of the device 10, liner 30 and cup 20. FIG. 3B is a cross-section of the device along the line A-A shown in FIG. 3A.

As can be seen from the Figures, the device 10 includes a first portion 2 and a second portion 4. The first portion 2 is configured to engage the liner 30. In the present example, the first portion 2 engages the liner 30 at an outer surface 31 of the liner 30. In particular, the first portion 2 can engage the surface 31 of the liner 30 at a location adjacent a rim 32 of the liner 30. This configuration can allow the liner to be positioned with respect to the device 10 such that a pole of the substantially hemispherical liner 30 is aligned with an axis of the device. The device axis is indicated by the dotted line labelled 18 in the Figures.

The first portion 2 of the device 10 is also configured to engage with a rim 22 of the acetabular cup 20. This can allow the device 10 to be positioned over the cup 20, while the liner 30 engaged by the first portion 2 also, such that the pole of the substantially hemispherical cup 20 is also aligned with the device axis 18. In this way, initial alignment of the poles of the cup 20 and the liner 30 with the device axis 18 can be achieved, in preparation for subsequent insertion of the liner 30 into the cup 20 as described in more detail below.

The first portion 2 can be suitably dimensioned to engage the surface 31 of the liner 30 and the rim 22 of the cup 20. In this embodiment, the first portion 2 includes at least three arms 6 for engaging the liner 30 and the rim 22 of the cup 20 at spaced apart points around the liner 30 and the rim 22. The arms 6 may comprise portions 7 that overhang the rim 22 of the liner 30 to engage the outer surface 31 of the liner 30. The overhanging portions 7 can form corners with a flat underside of the first portion 2, into which the liner 30 can be received. Distal ends of the overhanging portions 7 can engage the rim 22 of the cup 20. The size and shape of the arms 6 of the first portion 2 can be determined in accordance with the intended size of the liner 30 and the cup 20. As will be described below, in some embodiments, the lateral extent of the arms 6 of the first portion 2 may be adjustable, to accommodate liners and acetabular cups of different sizes.

In some embodiments, it is envisaged that the first portion 2 may include more than three arms 6. The provision of at least three arms 6 as shown in the Figures can provide a stable base for positioning of the device 10 on the cup 20, whereby the at least three points of contact between the first portion 2 and the cup 20 can prevent tilting of the first portion 2 with respect to the cup 20 while the liner 30 is inserted into the cup 20.

In some embodiments, the first portion 2 (for instance, the portions 7 described above) may be configured grip the surface 31 of the liner 30 to prevent the liner from coming loose from the device 10 while a surgeon initially aligns the device 10 and liner 30 with the cup 20.

The device 10 also includes a second portion 4 for pushing the liner 30 into the cup 20. The second portion includes a guide arrangement. In this embodiment, the guide arrangement has at least three guide members 8 for engaging the rim 32 of the liner 30 at spaced apart points around the rim 32. The guide members can extend outwardly from a central part 14 of the second portion 4. The central part 14 may be curved to conform to the shape of the inner surface of the liner 30. In the present embodiment, the second portion 4 includes three guide members 8. It is envisaged that more than three guide members may be provided. In some embodiments, the number of guide members 8 provided in the second portion 4 may be the same number as the number of arms 6 provided in the first portion 2.

In this embodiment, the guide members 8 of the second portion 4 engage the rim 32 of the liner 30 at three equally spaced points around the rim 32. This arrangement can allow the forces applied to the rim 32 by the second portion 4 to be balanced around the device axis 18, which may further reduce any tendency of the liner 30 to tilt as it is inserted into the cup 20. For similar reasons, the arms 6 of the first portion 2 engage the liner 30 and the rim 22 of the acetabular cup 20 at equally spaced points around the liner 30 and the rim 22 of the cup 20.

As shown in FIGS. 1-3, the guide members 8 and arms 6 in this embodiment are provided alternately around the device 10, at spaced apart points. This arrangement can provide a balanced configuration between the support provided by the arms 6 of the first portion 2 and the guidance and insertion forces provided by the guide members 8.

The guide members 8 engage with the rim 32 of the liner 30 to allow the second portion 4 of the device 10 to move linearly with respect to the first portion 2 along the device axis 18 for pushing the liner 30 into the cup 20. As with the arms 6 of the first portion 2, the guide members 8 of the second portion 4 may be suitably dimensioned for engagement with the rim 32 of a liner 30 of a given size. In some embodiments, the lateral extent of the guide members 8 from the device axis 18 may be adjustable, so that the device 10 can be used with liners and cups of different sizes.

The second portion 4 is coupled to the first portion 2 for linear movement of the second portion 4 with respect to the first portion 2 along the device axis 18. In the present embodiment, the coupling between the first portion 2 and the second portion 4 is provided by a guide sleeve 12 and a rod 42. The rod 42 is slidably mounted within the guide sleeve 12 for linear movement within the guide sleeve 12 along the device axis 18. In this example, the rod 42 and guide sleeve 12 are positioned towards a centre of the device 10. The central location of the rod 42 and guide sleeve 12 can prevent tilting of the device 10 as a force is applied to the second portion 4 for inserting the liner 30.

In the present embodiment, the rod 42 is provided as part of the second portion 4, while the guide sleeve 12 is provided as part of the first portion 2. However, it is envisaged that this configuration could be reversed, so that a rod 42 may be provided as part of the first portion 2 and a guide sleeve 12 may be provided as part of the second portion 4.

In this embodiment, the device 10 includes a button 40 for manually pushing the second portion 4 along the device axis 18. The button 40 can, in use, be pressed using a finger or thumb. The force applied to the button 40 can act to push the second portion 4 along the device axis 18 such that the guide members 8 of the second portion 4 bear down on the rim 32 of the liner 30, thereby pushing the liner 30 into the cup 20. FIG. 1A shows the position of the liner 30 and the second portion 4 of the device 10 before the liner 30 has been inserted into the cup 20. In this example, the button extends upwardly from a proximal end of the rod 42 received within the guide sleeve 12. FIG. 2A shows the position of the liner 30, second portion 4 and button 40 after the button 40 has been pressed to push the liner 30 into the cup 20. As can be seen from the example in FIG. 2A, after the liner 30 has been inserted, the rim 32 of the liner 30 may be substantially flush with the rim 22 of the cup 20.

In this example, the guide sleeve 12 extends into the space defined by the inner surface of the liner 30. The length of the guide sleeve 12 can be chosen in accordance with the degree of stability that is required for preventing tilting of the rod 42 within the guide sleeve 12. For instance, it is envisaged that the guide sleeve 12 may also extend proximally (away from the liner 30 and cup 20) so that its overall length may be increased. As will be described in more detail below, the outer surface of the guide sleeve 12 may provide a surface for holding onto the device 10 while the button 40 is pressed to insert the liner 30 into the cup 20.

In an alternative embodiment, it is envisaged that instead of a button of the kind shown in FIGS. 1 to 3, the second portion 4 may be provided with a connection means (for example, a female or male connector) for connecting the second portion 4 to a tool for applying force to the second portion 4 along the device axis 18. The connection means can be provided at a location substantially corresponding to the location of the button 40 shown in the Figures. The tool can, for example, comprise a rod with a handle for gripping the tool while pressing down on the second portion 4. A distal end of the tool can include a connector corresponding to the connection means of the second portion.

As noted above, the guide members 8 of the second portion 4 can act to guide the liner 30 as it is inserted into the cup 20. In the present embodiment, the guide members 8 exert all of the force required to insert the liner 30 into the cup. However, it is envisaged that in alternative embodiments the second portion 4 may include further features for applying a force to the liner 30. For instance, it is envisaged that the second portion 4 may include an engagement member for engaging an inner surface of the liner 30, at a pole of the liner 30, for pushing the liner 30 into the cup 20. The engagement member may extend downwardly from the rod 42 to engage with the pole of the liner 30. In such examples, the application of the force at the pole of the liner 30 can minimise the risk of tilting of the liner 30 as it is inserted. The guide members 8 can act to further minimise the risk of tilting of the liner 30 by engaging the rim 32 of the liner 30. Note that the 8 in such examples would themselves also provide at least some of the force for inserting the liner 30 into the cup 20, although it is envisaged that the primary force would be applied using the engagement member.

In the examples described herein, both the liner 30 and the acetabular cup 20 are substantially hemispherical. As seen most clearly in FIGS. 1B and 2B, the cup 20 may be provided with one or more openings such as that shown at 40 the pole of the cup 20 in FIG. 1B. These openings can be used to insert pins or screws for mounting the cup 20 in the acetabulum of a patient. The mounting of the liner 30 within the cup 20 is generally achieved using a taper lock. This arrangement is well known in the art and will not be elaborated upon here in any detail. The taper lock is located at the surfaces of the liner 30 and cup 20 adjacent their respective rims 32, 22.

FIGS. 4A to 4B each illustrate a device according to an embodiment of this invention. In these embodiments, the configuration and operation of the device 10 is similar to that described above in relation to FIGS. 1 to 3. However, in the embodiments of FIGS. 4A to 4E, the device 10 is provided with one or more gripping surfaces 50. These gripping surfaces 50 can allow the device 10 to be manually gripped by a surgeons fingers or thumbs, while the liner 30 is inserted into the cup 20. These gripping surfaces 50 can thus allow the device 10 to be held steady during use. For instance, it is envisaged that a surgeon using the device 10 may manually grip the device 10 at the gripping surfaces 50 with one hand, while using the other hand to either press the button 40 shown in FIGS. 4A to 4E or alternatively to operate a tool connected to the second portion 4 of the device 10 as described above.

In FIG. 4A, the guide sleeve 12 of the device 10 extends in a proximal direction (i.e. towards the user 10 of the device) away from the arms 6 of the first portion 2. The gripping surfaces 50 in this example are provided on the outer sides of the guide sleeve 12. In this example, the gripping portions 50 have a faceted configuration, with one or more facets being located around the outer surface of the guide sleeve 12. Each facet can itself have a profiled surface to allow the device 10 to be held securely between a finger and thumb of the surgeon.

In the example of FIG. 4B, the gripping surfaces 50 are provided on a pedestal 54 that extends upwardly from one of the arms 6 of the first portion 2. The gripping surfaces 50 are provided on opposite sides of the pedestal 54, to allow the pedestal 54 to be pinched between, for instance, a finger and thumb or the index finger and middle finger of the surgeon.

In the example of FIG. 4C, the gripping surfaces 50 comprise a series of ridges located on an outer surface of the guide sleeve 12. Note that in the example of FIG. 4C, further gripping surfaces may also be provided on upstanding vanes 56 that are located on an upper surface of the arms 6 of the first portion 2. A respective vane 56 may be provided on each arm 6. It is envisaged that vanes 56 of the kind shown in FIG. 4C may also be provided in the embodiments of FIGS. 4A, 4B, 4D and 4E.

In the example of FIG. 4D, the gripping surfaces 50 are located again on an outer surface of the guide sleeve 12 of the device 10. However, the gripping surfaces 50 in the example of FIG. 4D comprise a plurality of ridges that run parallel to the device axis.

In the example of FIG. 4E, the guide sleeve 12 forms a gripping portion 58 that extends upwardly from the device 10, away from the arms 6 of the first portion 2. In this example, the gripping portion 58 includes three facets. The gripping surfaces 50 in each facet may be held onto by the surgeon (for instance, using a thumb to grip one of the facets of the gripping portion 58 while using respective fingers to hold on to the gripping surfaces 50 of the other two facets of the gripping portion 58.

FIGS. 5 and 6 show a device for inserting a liner into an acetabular cup in accordance with another embodiment of the invention. In this embodiment, the arms 6 of the first portion 2 and the guide members 8 of the second portion 4 of the device 10 are adjustable for varying a lateral distance of the arms 6 and the guide members 8 from the device axis 18, according to the size of the cup and liner 30 that is to be used. This can allow the device 10 to be used with liners 30 and acetabular cups of different sizes.

Figure 5A:
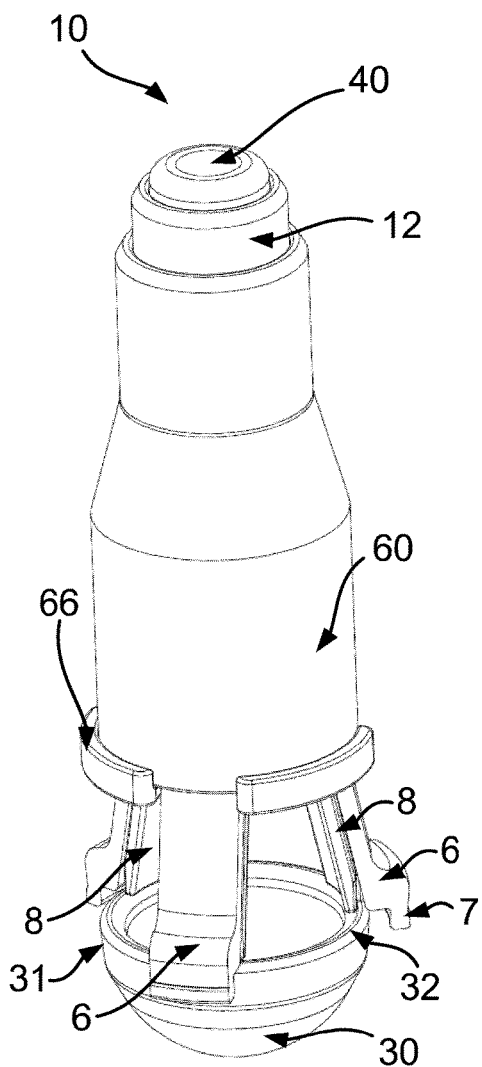
FIG. 5A shows a device for inserting a liner into an acetabular cup in accordance with a further embodiment of the invention.
Figure 5B:
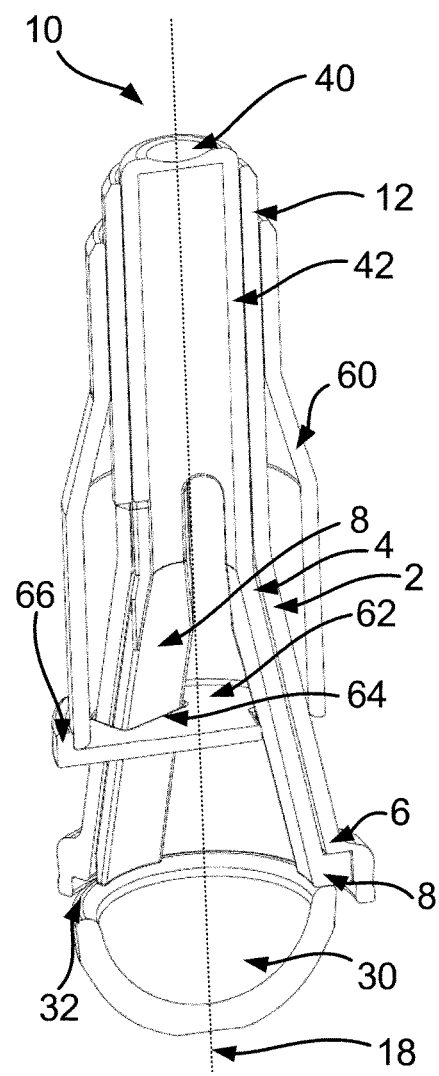
FIG. 5B is a cut-away view of the device of FIG. 5A.
Figures 6A, 6B:
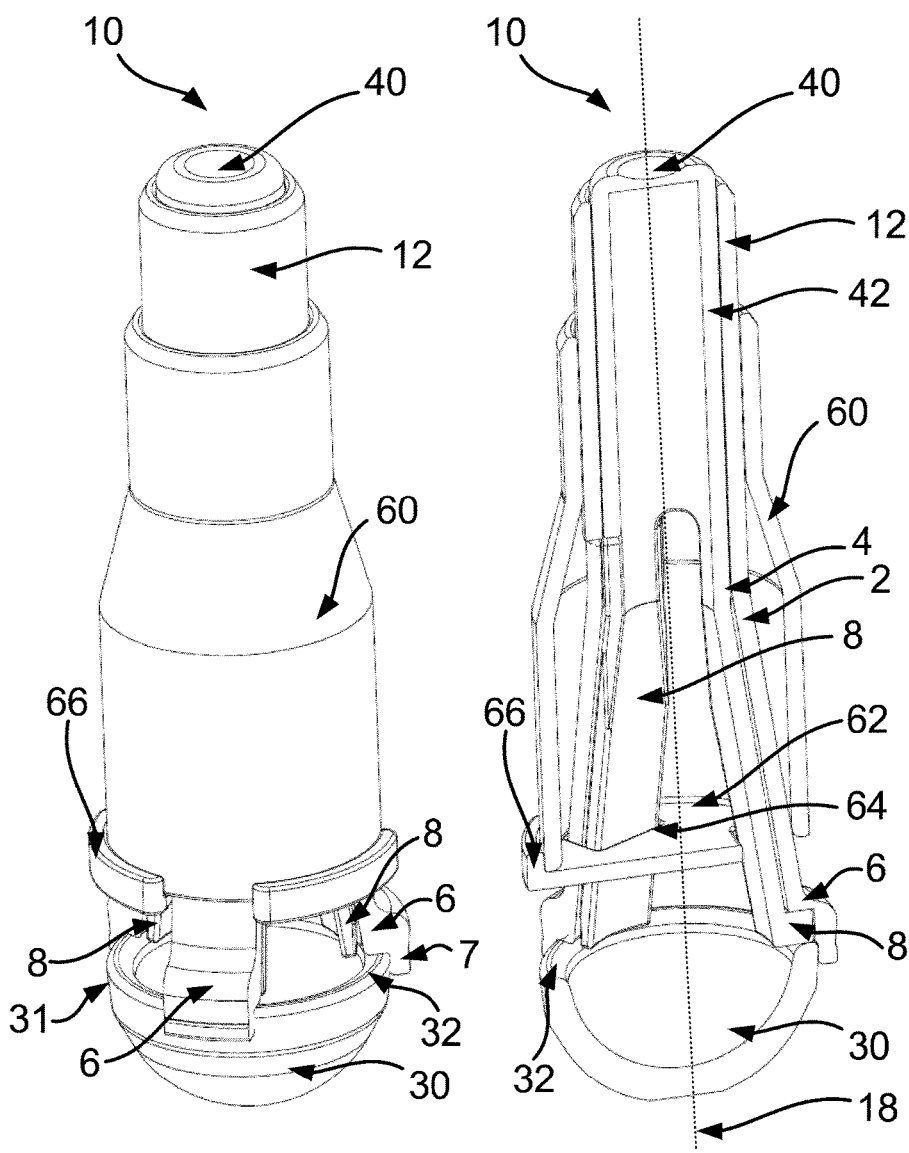
FIG. 6A shows the device of FIG. 5A, after the liner has been inserted into the cup.
FIG. 6B is a cut-away view of the device in FIG. 6A.

FIG. 5A shows the device 10 in a first position, prior to adjustment of the arms 6 and guide members 8 for engagement with the liner 30. FIG. 6A shows the device 10 in a second position, after the arms 6 and guide members 8 have been adjusted according to the size of the liner 30. FIGS. 5B and 6B shown cutaway views of the device positions shown in FIGS. 5A and 6A, respectively.

In this embodiment, in common with the embodiment of FIGS. 1 to 3, the device 10 includes a first portion 2 that has at least three arms 6 for engaging the liner 30 and a rim of an acetabular cup (the cup is not shown in FIG. 5 or 6) at spaced apart points around the liner 30 and the rim of the cup. The device 10 also includes a second portion 4 for pushing the liner 30 into the cup. The second portion 4 has three guide members 8 for engaging a rim 32 of the liner 30 at spaced apart points around the rim 32. Again, the second portion 4 is coupled to the first portion 2 for linear movement of the second portion 4 with respect to the first portion 2 along the device axis 18. Again, in this embodiment the coupling between the first portion 2 and the second portion 4 is implemented by means of a guide sleeve 12 within which is received a rod 42. The guide sleeve 12 in this embodiment is formed as part of the first portion 2, while the rod 42 is formed as part of the second portion 4. Also in common with the previously described embodiments, the device 10 includes a button 40 that is located at a proximal end of the rod 42 for pushing the second portion 4 down onto the liner 30 for pushing the liner 30 into an acetabular cup. Once again, the button 40 may be replaced with connections means as noted above.

The operation of the device 10 for varying the lateral distance of the arms 6 and guide members 8 of the device 10 from the device axis 18 will be described below.

The arms 6 of the first portion 2 and the guide members 8 of the second portion 4 extend at an acute angle with respect to the device axis 18. The angle at which the arms 6 and guide members 8 may extend with respect to the device axis 18 may be in the range 10-30°. The device 10 in this embodiment also includes an outer sleeve 60 which at least partially encloses the first portion 2 and the second portion 4. In use, the outer sleeve 60 is configured to adjust the positions of the arms 6 and guide members 8 by sliding along the device 10 in a direction generally parallel to the device axis 18 to push the arms 6 and guide members 8 inward toward the device axis.

In some examples, an inner surface of the sleeve 60 around an edge of an opening at a distal end of the sleeve 60 can ride against the outer surfaces of the arms 6 and/or guide members 8 to push the arms 6 and/or guide members 8 inwards. In this embodiment, however, the outer sleeve 60 is further provided with a plate 62 which may be located at a distal end of the outer sleeve 60 and which may include one or more slots 64 within which the arms 6 and/or guide members 8 are received. These slots 64 can restrict movement of the arms 6 and/or guide members 8 and the edges of the slots 64 can push against the arms 6 and/or guide members 8 to adjusting their position as the outer sleeve 60 is moved along the device axis 18. A rim 66 of the plate 62 can engage with an outer surface of a cylindrical portion of the outer sleeve 60 to secure the plate 62.

As can be seen in FIGS. 5 and 6, instead of having an alternating configuration around the rim of the liner 30 and cup as shown in the earlier embodiments, the guide members 8 in this example may be located adjacent the arms 6 so that as the arms 6 are pushed by the outer sleeve 60 towards the device axis 18, the arms 6 push against the guide members 8 so that the guide members 8 are also pushed towards the device axis 18. In some examples, the arms 6 and the guide members 8 may be coupled together with a tongue and groove type coupling running along their length to inhibit or prevent rotation of the arms 6 with respect to the guide members 8 around the device axis 18.

The operation of the outer sleeve 60 for adjusting the lateral extent of the arms 6 and guide members 8 with respect to the device axis 18 can be seen by comparing the positions of the outer sleeve 60, arms 6 and guide members 8 shown in FIGS. 5A and 5B (i.e. prior to adjustment of the arms 6 and guide members 8) with their positions in FIGS. 6A and 6B (i.e. after the arms 6 and guide members 8 have been adjusted). In this example, as the outer sleeve 60 is moved from a proximal position shown in FIGS. 5A and 5B to a distal position shown in FIGS. 6A and 6B, the outer sleeve 60 urges the arms 6 and guide members 8 inward towards the rim 32 of the cup 30 until the arms 6 and guide members 8 engage with the cup 30. In this way, the device 10 can be used with liners 30 and acetabular cups of various different sizes.

In some embodiments, there can be provided a kit comprising a device of the kind described herein and a liner. The kit may also include an acetabular cup. In some examples, the kit may include liners and/or acetabular cups of various sizes. In such examples, the device may be a device having arms and guide members that are adjustable as described above in relation to FIGS. 5 and 6.

The device 10 and its various component parts can be formed from a polymer. The polymer used should be able to withstand temperatures associated with sterilisation procedures and should also should be sufficiently rigid to withstand the forces associated with the operation of the device for inserting a liner into an acetabular cup. It is envisaged that suitable polymers for constructing a device of the kind described herein include acetals, nylons or sulfone polymers. In one example, Polyether ether ketone (PEEK) may be used. It is also envisaged that the materials (e.g. polymer) used to manufacture the device may include radiopaque materials, to allow the device to be viewed in X-rays taken during a hip replacement procedure. For instance, it is envisaged that a polymer including Barium Sulphate as a radio-opacifier may be used.

Figure 7A:
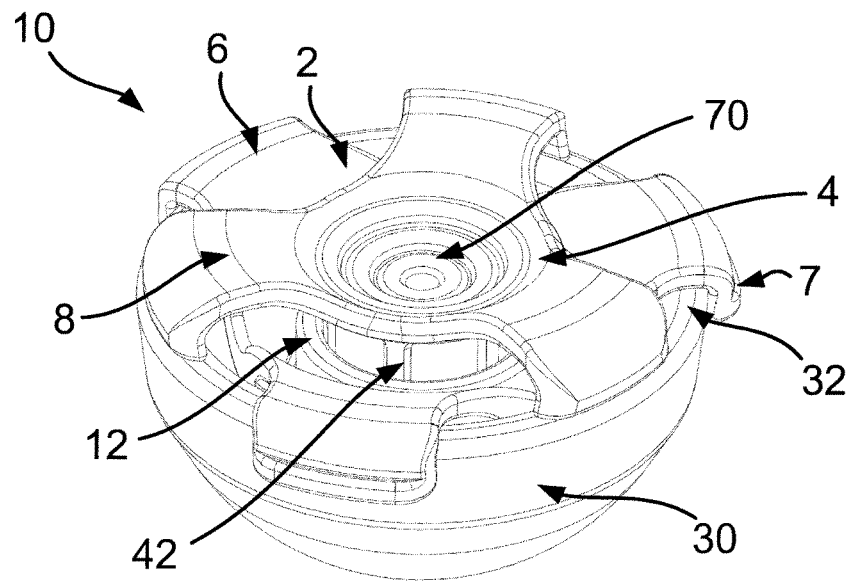
FIG. 7A shows a device for inserting a liner into an acetabular cup in accordance with another embodiment of the invention.
Figure 7B:
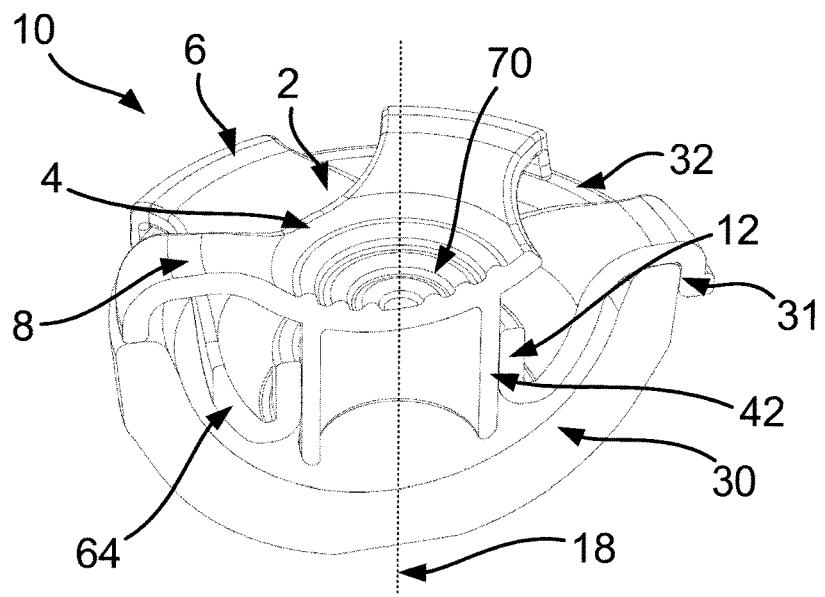
FIG. 7B is a cut-away view of the device of FIG. 7A.

FIG. 7A shows a device for inserting a liner into an acetabular cup in accordance with a further embodiment of this invention. FIG. 7B is a cutaway view of the device shown in FIG. 7A. The device 10 in FIG. 7 is similar in some respects to the device shown in FIG. 1. The device 10 includes a first portion 2 that is configured to engage a liner 30 and a rim of an acetabular cup (the cup is not shown in FIG. 7A or 7B) in much the same way as described above. The device 10 also includes a second portion 4 for pushing the liner 30 into the cup. Again, the second portion 4 has at least three guide members 8 for engaging a rim 32 of the liner 30.

The second portion 4 can include a button 70 for manually pushing a second portion 4 along the device axis 18 as explained above. The second portion 4 can alternatively be provided with connection means for connecting to a tool for applying a force to the second portion 4. As shown in FIGS. 7A and 7B, the button 70 may be provided with a series of ridges forming concentric rings, which can provide the surgeon with tactile feedback as to the position of the center of the button 70.

The device 10 in this example also includes a coupling between the first portion 2 and the second portion 4 that comprises a guide sleeve 12 and a rod 72. The rod 72 is formed as part of the second portion 4, while the guide sleeve 12 is formed as part of the first portion 2.

The main difference between the embodiment shown in FIG. 7 and the embodiment shown in FIG. 1 is that the embodiment of FIG. 7 the second portion 4 is located above the first portion 2. The guide members 8 extend above the first portion 2, so that the first portion 2 is located generally between the guide members 8 of the second portion 4 and the liner 30. This configuration may allow the second portion 4 to be viewed more clearly by a surgeon using the device 10 compared to, for instance, the embodiment shown in FIG. 1, since the second portion 4 and its guide members 8 are not obscured by the first portion 2. The surgeon may therefore have a clearer view of the position of the second portion 4 and the liner 30 as he or she is pushing down on the second portion 4 for inserting the liner 30.

FIG. 8 shows a device for inserting a liner into an acetabular cup in accordance with another embodiment of this invention. FIG. 8B is a cutaway view of the device 10 shown in FIG. 8A.

In this embodiment, in common with the embodiment described above in relation to FIG. 7, the second portion 4 is located above the first portion 2 so that the guide members 8 extend over the first portion 2.

In the embodiment of FIG. 8, the first portion 2 is coupled to the second portion 4 for linear movement of the second portion 4 with respect to the first portion 2 along the device axis 18 using a coupling comprising a guide sleeve 12 and a rod 42. However, in the example of FIG. 8, the second portion 4 of the device 10 is movable along the device axis 18 by holding the second portion 4 around the outer surface of the guide sleeve 12 and/or using one or more vanes 56 or other gripping surfaces of the kind described above, and pushing down on the second portion 4 while the rod 42 that is formed as part of the first portion 2 remains substantially stationary with respect to the acetabular cup. In the device of FIG. 8, the length of the rod 42 and the guide sleeve 12 can be relatively long (i) to allow for increased stability of the device 10 for linear movement of the second portion 4 without tilting with respect to the first portion, and (ii) to provide a relatively large surface area for allowing the surgeon to hold on to the second portion 4 while it is being pushed downwards to insert the liner 30 into the cup.

A method for inserting a liner into an acetabular cup can include first providing an insertion device of the kind described herein and then mounting a liner on the device so that a first portion of the device is engaged with the liner. Next, the device with the liner engaged with the first portion can be positioned so that the liner is partially received within an acetabular cup and so that the first portion of the device engages with a rim of the cup. As explained above, this initial alignment step can align a pole of the liner and a pole of the cup along an axis of the device. Once the device and liner have been positioned in this way, the device can be operated to push the liner along the device axis into the cup as described above.

The method can also include adjusting the positions of the arms of the first portion of the insertion device and the guide members of the second portion of the insertion device according to the size of the cup and the liner. The method can further include pressing a button of the second portion in order manually to push the second portion along the device axis to insert the cup. Alternatively, the method can include connecting a tool to the second portion to apply a force to the second portion to push the second portion along the device axis to insert the cup as also explained above. The method can further include manually gripping the device at one or more gripping surfaces of the kind described in relation to, for example, FIGS. 4A to 4E.

In some embodiments, the device may include features for preventing re-use after the liner has been inserted in the cup. These features may include non-return members that can act to block movement of the second portion with respect to the first portion, once the liner has been inserted. Two example implementations including features of this kind are described below in relation to FIGS. 9 and 10.

Figure 9:
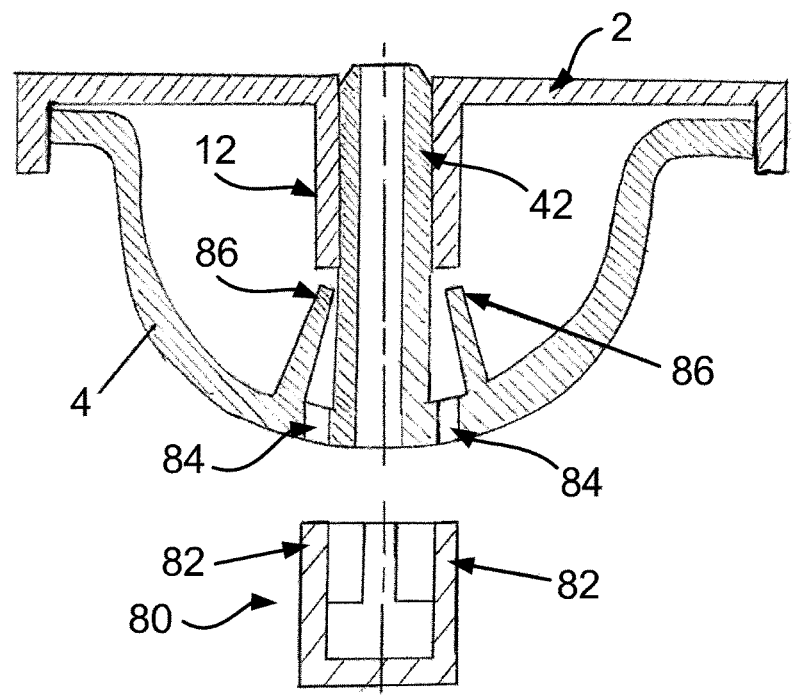
FIG. 9 shows a device for inserting a liner into an acetabular cup in accordance with another embodiment of the invention.

FIG. 9 shows a device according to an embodiment of the invention. As described above, the device includes a first portion 2 and a second portion 4, a guide sleeve 12 and a rod 42. In this embodiment, the non-return members take the form of one or more flexible arms 86. The flexible arms 86 may be incorporated into the second portion 4 as shown in FIG. 9. It is envisaged that in embodiments in which the guide sleeve 12 is a part of the second portion 4 and in which the rod 42 is a part of the first portion 2, the flexible arms 86 may instead be incorporated into the first portion 2.

The arms 86 can extend inwardly, toward the axis 18 of the device, so that in an initial position of the device, prior to insertion of the liner into the cup, they urge against an outer surface of the guide sleeve 12. A plurality of such flexible arms 86 may be located at spaced apart points around the guide sleeve 12. The arms 86 may be regularly spaced around the guide sleeve 12 so as to prevent tilting of the second portion 4 with respect to the first portion 2 that may otherwise be caused by the forces exerted on the guide sleeve by the arms 86.

As the second portion 4 is moved with respect to the first portion 2 to insert the liner as described above, the tips of the arms 86 may slide along the outer surface of the guide sleeve 12 until they reach the end of the guide sleeve. The length of the guide sleeve 12 may be chosen so that the arms 86 slide off the end of the guide sleeve 12 as the liner becomes fully inserted in the cup.

When the arms 86 slide off the ends of the guide sleeve 12, they move inwards towards the device axis 18 to reach the configuration shown in FIG. 9. In this configuration, the first portion 2 and the second portion 4 cannot return to their initial position, since movement of the second portion 4 with respect to the first portion 2 to retract the rod 42 along the guide sleeve 12 is blocked by the arms 86. This can prevent the device from being re-used.

In one embodiment, the device may include one or more apertures 84 for receiving a tool 80 to splay the arms 86 apart to receive the guide sleeve 12 during assembly of the device (e.g. during manufacture). The apertures 84 may be provided either in the first portion 2 or the second portion 4. The apertures 84 may be located opposite the guide sleeve 12 so as to allow the fingers 82 of the tool 80 to access the flexible arms 86 to push them aside (splay them) so that the guide sleeve 12 can be received between them.

Figure 10:
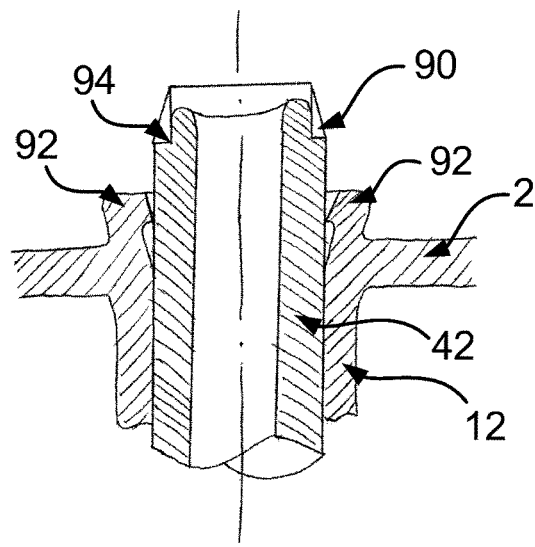
FIG. 10 shows a device for inserting a liner into an acetabular cup in accordance with a further embodiment of the invention.

FIG. 10 shows a device according to a further embodiment of the invention. In this embodiment, the device includes a guide sleeve 12 with a rod 42 slidably received therein for coupling the first portion 2 and the second portion. In this embodiment, the guide sleeve 12 is part of the second portion 2 while the rod 42 is part of the first portion 2 although, as described above, it is envisaged that this arrangement can be reversed.

The non-return members in this embodiment include one or more collet fingers 92 comprised in the guide sleeve 12. The rod 42 includes an opening 94 for receiving the collet fingers 92 as the liner is inserted into the cup. The collet finger 92 can form a snap-fit with the opening 94, to prevent further movement of the rod 42 within the guide sleeve 12. This can prevent the device from being re-used.

In FIG. 10, the opening 94 is shown to be located at one end of the rod 42, however it is envisaged that the opening 94 may comprise a slot located on an outer surface of the rod 42 at some intermediate point along its length. The positions of the collet finger 92 and the opening 94 can be chosen so that the collet fingers 92 are received in the opening 94 as the liner becomes fully inserted in the cup.

In some embodiments, a cap 90 may be used during assembly of the device (e.g. during manufacture) to allow the rod 42 in be inserted into the guide sleeve 12 without allowing the collet fingers 92 to snap into the opening 94. Once the rod 42 is correctly inserted, the cap 90 may be discarded prior to shipping.

FIGS. 11 to 14 show various views of a device 10 for inserting a liner 30 into an acetabular cup 20 in accordance with a further embodiment of the invention. This device 10 in this embodiment is similar in some respects to the device described above in relation to FIGS. 1 to 3.

FIGS. 11A and 12A show the device 10 in an initial position, prior to insertion of the liner 30 into the acetabular cup 20, while FIGS. 13A and 14A show the device 10 after the liner 30 has been inserted into the cup 20. FIGS. 11B and 13B are cross-sections of the device 10 along the line A-A shown in FIGS. 11A and 13A, respectively. FIGS. 12B and 14B are cutaway views of the device 10, liner 30 and cup 20 in the positions shown in FIGS. 12A and 14A, respectively.

As with the above described examples, the device 10 in this embodiment includes a first portion 2 and a second portion 4. The first portion 2 is configured to engage the liner 30 at an outer surface 31 of the liner 30. In particular, the first portion 2 can engage the surface 31 of the liner 30 at a location adjacent a rim 32 of the liner 30. As with the examples of FIGS. 1 to 3, this configuration can allow the liner 30 to be positioned with respect to the device 10 such that a pole of the substantially hemispherical liner 30 is aligned with the device axis 18 of the device 10.

The first portion 2 of the device 10 is also configured to engage with a rim 22 of the acetabular cup 20. This can allow the device 10 to be positioned over the cup 20, while the liner 30 engaged by the first portion 2 also, such that the pole of the substantially hemispherical cup 20 is also aligned with the device axis 18. In this way, initial alignment of the poles of the cup 20 and the liner 30 with the device axis 18 can be achieved, in preparation for subsequent insertion of the liner 30 into the cup 20 as described previously.

The first portion 2 can be suitably dimensioned to engage the surface 31 of the liner 30 and the rim 22 of the cup 20. Again in this embodiment, the first portion 2 includes at least three arms 6 for engaging the liner 30 and the rim 22 of the cup 20 at spaced apart points around the liner 30 and the rim 22. The arms 6 may comprise portions 7 that overhang the rim 22 of the liner 30 to engage the outer surface 31 of the liner 30. The overhanging portions 7 can form corners with a flat underside of the first portion 2, into which the liner 30 can be received. Distal ends of the overhanging portions 7 can engage the rim 22 of the cup 20. The size and shape of the arms 6 of the first portion 2 can be determined in accordance with the intended size of the liner 30 and the cup 20.

As described previously, it is envisaged that the first portion 2 may include more than three arms 6. The provision of at least three arms 6 as shown in FIGS. 11 to 16 can provide a stable base for positioning of the device 10 on the cup 20, whereby the at least three points of contact between the first portion 2 and the cup 20 can prevent tilting of the first portion 2 with respect to the cup 20 while the liner 30 is inserted into the cup 20.

In some embodiments, the first portion 2 (for instance, the portions 7 described above) may be configured grip the surface 31 of the liner 30 to prevent the liner from coming loose from the device 10 while a surgeon initially aligns the device 10 and liner 30 with the cup 20. Note that in this embodiment, the distal ends of the overhanging portions 7 each include outwardly facing gripping surfaces 50 to assist the surgeon in holding on to the device 10.

The device 10 also includes a second portion 4 for pushing the liner 30 into the cup 20. The second portion includes a guide arrangement. As with the example of FIGS. 1 to 3, the guide arrangement in the present embodiment has at least three guide members 8. The guide members can extend outwardly from a central part 14 of the second portion 4. The central part 14 in this example forms an engagement member having a curved outer surface (e.g. substantially hemispherical) for conforming with the shape of the inner surface of the hemispherical liner 30. The engagement member may extend downwardly from a rod 42 of the second portion 4, to engage with the pole of the liner 30. The engagement member can engage an inner surface of the liner 30, at least at a pole of the liner 30, for pushing the liner 30 into the cup 20. The application of the force at the pole of the liner 30 can minimise the risk of tilting of the liner 30 as it is inserted. Note that in the present example the engagement member formed by the central portion 14 engages not only the pole of the liner but also the parts of the liner 30 that surround the pole, increasing the contact surface area between the engagement member and the liner 30.

In this embodiment, the guide members 8 of the second portion 4 can engage the rim 32 of the liner 30 at three equally spaced points around the rim 32. As can be seen in FIG. 11B, in the initial position, prior to insertion of the liner 30 into the cup 20, there is a gap 5 between an underside of the guide members 8 and the rim 32 of the liner 30. In the present embodiment, the force for inserting the liner 30 into the cup 20 is applied to the liner 30 primarily through the curved outer surface of the engagement member formed by the central part 14 of the second portion 4. The relatively large surface area of contact between the curved outer surface of the central part 14 and the inner surface of the liner 30 can allow the insertion force to be transferred to the liner 30 effectively. Note that in the initial position shown in FIGS. 11 and 12, the curved outer surface of the central part 14 and the inner surface of the liner 30 are already in contact, so that as the second portion begins to move along the device axis 18 relative to the first portion 2, the liner 30 may immediately start to be inserted into the cup 20.

The gap 5 may generally be a relatively small gap, for instance in the gap may be smaller than 0.5 mm (e.g. more particularly in the range 0.1 mm to 0.5 mm), so that if, as the liner 30 is being inserted into the cup 20, the liner 30 begins to tilt relative to the device axis 18, only a small amount of such tilting may occur before one or more of the guide members 8 make contact with the rim 32 of the liner 30, to prevent further tilting. Accordingly, in this embodiment, the guide arrangement, including the arms 8, may act primarily to engage the rim of the liner to prevent (e.g. significant) tilting of the liner 30 as it inserted into the cup 20, while the central part 14 of the second portion 4 may act to apply the insertion force.

As with the example of FIGS. 1-3, the guide members 8 and arms 6 in this embodiment are provided alternately around the device 10, at spaced apart points. This arrangement can provide a balanced configuration between the support provided by the arms 6 of the first portion 2 and the guidance provided by the guide members 8.

As with the arms 6 of the first portion 2, the guide members 8 of the second portion 4 may be suitably dimensioned for engagement with the rim 32 of a liner 30 of a given size. Again, it is envisaged that the lateral extent of the guide members 8 from the device axis 18 may be adjustable, so that the device 10 can be used with liners and cups of different sizes.

As with the example of FIGS. 1 to 3, the second portion 4 is coupled to the first portion 2 for linear movement of the second portion 4 with respect to the first portion 2 along the device axis 18. In the present embodiment, the coupling between the first portion 2 and the second portion 4 is provided by a guide sleeve 12 and a rod 42. The rod 42 is slidably mounted within the guide sleeve 12 for linear movement within the guide sleeve 12 along the device axis 18. In this example, the rod 42 and guide sleeve 12 are positioned towards a centre of the device 10. The central location of the rod 42 and guide sleeve 12 can prevent tilting of the device 10 as a force is applied to the second portion 4 for inserting the liner 30.

In the present embodiment, the rod 42 is provided as part of the second portion 4, while the guide sleeve 12 is provided as part of the first portion 2. However, it is envisaged that this configuration could be reversed, so that a rod 42 may be provided as part of the first portion 2 and a guide sleeve 12 may be provided as part of the second portion 4. In such examples, the engagement member having the curved outer surface for engaging with the inner surface of the liner 30 may extend downwardly from the guide sleeve 12 instead of from the rod 42 as described in relation to the present embodiment. Note that in the present example, the rod 42 may comprise a substantially solid cylinder, instead of the substantially hollow cylinder included in the example of FIGS. 1 to 3.

As with the embodiment of FIGS. 1 to 3, in the present embodiment, the device 10 includes a button 40 for manually pushing the second portion 4 along the device axis 18. The button 40 can, in use, be pressed using a finger or thumb. A force applied to the button 40 can act to push the second portion 4 along the device axis 18 such that the curved outer surface of the engagement member of the central part 14 bears down on the inner surface of the liner 30, thereby pushing the liner 30 into the cup 20. In this example, the button 40 extends upwardly from a proximal end of the rod 42 received within the guide sleeve 12.

FIGS. 13 and 14 show the position of the liner 30, second portion 4 and button 40 after the button 40 has been pressed to push the liner 30 into the cup 20. As can be seen from the example in FIG. 14A, after the liner 30 has been inserted, the rim 32 of the liner 30 may be substantially flush with the rim 22 of the cup 20.

In this example, the guide sleeve 12 extends into the space defined by the inner surface of the liner 30. The length of the guide sleeve 12 can be chosen in accordance with the degree of stability that is required for preventing tilting of the rod 42 within the guide sleeve 12. For instance, it is envisaged that the guide sleeve 12 may also extend proximally (away from the liner 30 and cup 20) so that its overall length may be increased. As described previously, the outer surface of the guide sleeve 12 may provide a surface for holding onto the device 10 while the button 40 is pressed to insert the liner 30 into the cup 20.

As described previously, it is envisaged that instead of a button 40 of the kind shown in FIGS. 11 to 14, the second portion 4 may be provided with a connection means (for example, a female or male connector) for connecting the second portion 4 to a tool for applying force to the second portion 4 along the device axis 18. The connection means can be provided at a location substantially corresponding to the location of the button 40 shown in the Figures. The tool can, for example, comprise a rod with a handle for gripping the tool while pressing down on the second portion 4. A distal end of the tool can include a connector corresponding to the connection means of the second portion.

Figure 15A:
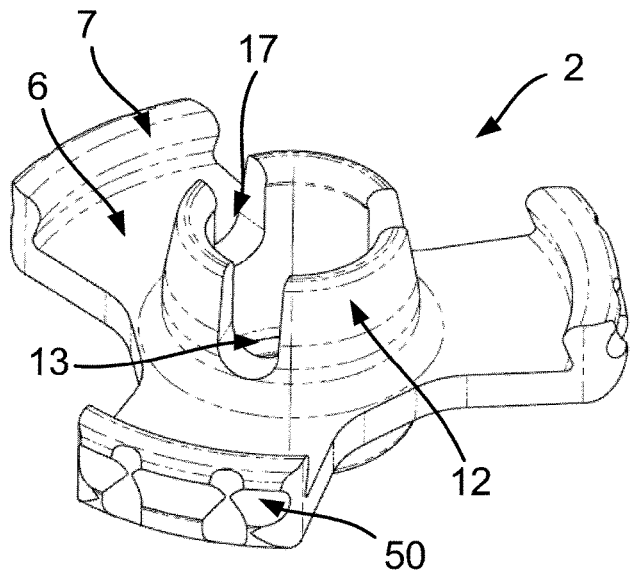
FIG. 15A shows the underside of the first portion of the device shown in FIGS. 11 and 12.
Figure 15B:
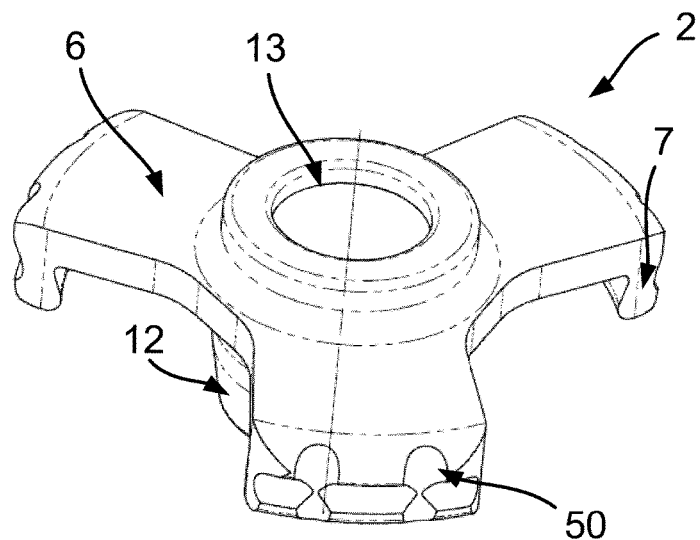
FIG. 15B shows the top side of the first portion of the device shown in FIGS. 11 and 12.
Figure 15C:
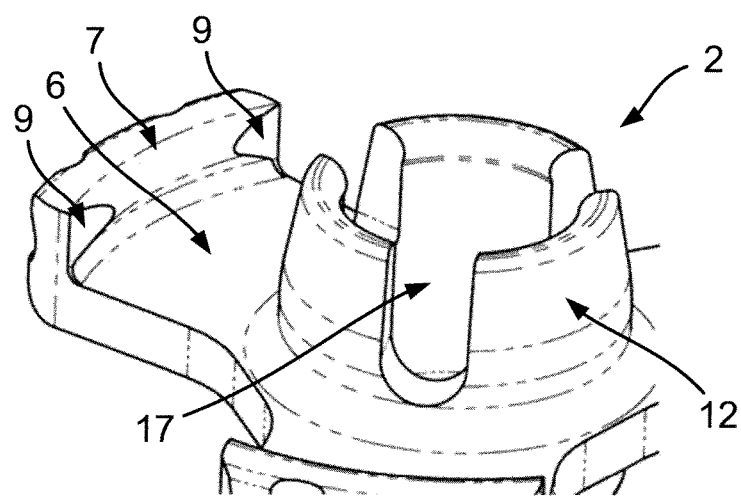
FIGS. 15C and 15D each show an optional modification to the underside of a first portion of the device shown in FIGS. 11 and 12.
Figure 15D:
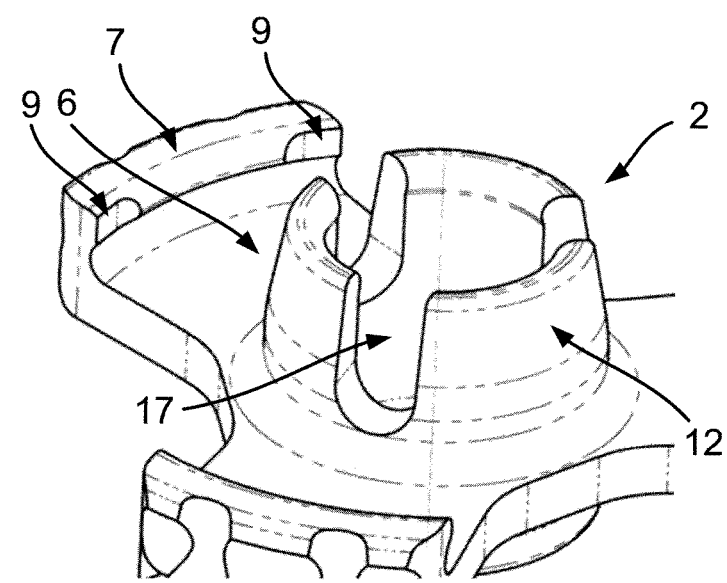
Figure 16B:
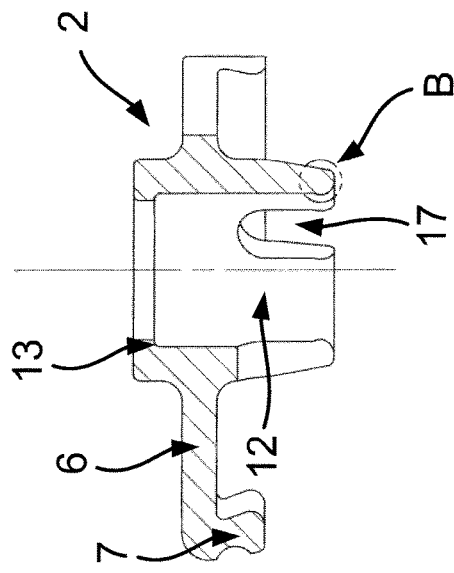
FIG. 16B shows a cross section of the first portion of the device shown in FIGS. 11 and 12.
Figure 16C:
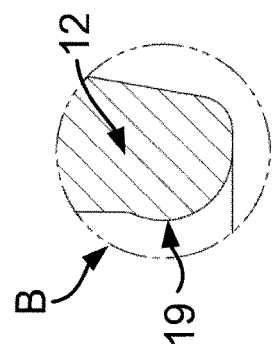
FIG. 16C shows a detail of the first portion shown in FIG. 16B.
Figure 16A:
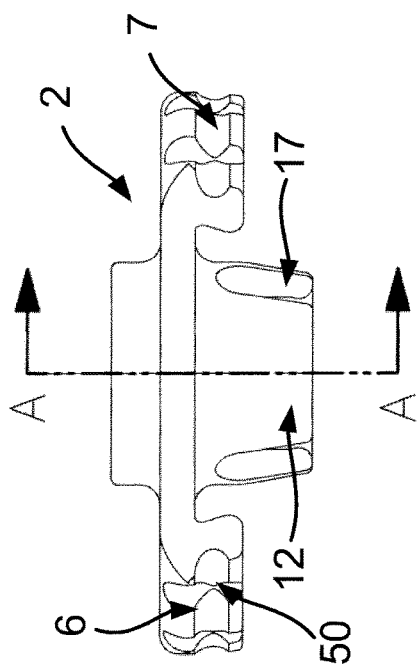
FIG. 16A shows a side view of the first portion of the device shown in FIGS. 11 and 12.

FIGS. 15 and 16 show a number of views of the first portion 2 of the device 10 of FIGS. 11 to 14. In particular, FIG. 15A shows the underside of the first portion 2 which, in use, faces the interior of the liner 30, FIG. 15B shows the top side of the first portion 2 which, in use, faces away from the liner 30, FIG. 16A shows a side view of the first portion 2, FIG. 16B shows a cross section of the liner 30 through the line A-A shown in FIG. 16A, and FIG. 16C shows a detail of the sleeve 12 of the first portion 2.

As can be seen in, for example, FIG. 16B, an inner surface of the sleeve 12 includes, at a proximal opening thereof, an annular lip 13 which extends inwardly towards the device axis 18. With reference to FIG. 14B, it can be seen that the rod 42 includes a ridge 41 on an outer cylindrical surface thereof. In the present example, the ridge 41 on the rod 42 is formed by a step change (increase) in the diameter of the rod 42 at a point intermediate a proximal and distal end of the rod 42. The lip 13 and the ridge 41 may cooperate to prevent inadvertent reverse mounting (i.e. with the overhanging portions 7 extending proximally instead of distally) of the first portion on the second portion 4, since the lip 13 may abut the ridge 41, to prevent the rod 42 from passing through the sleeve 12. For instance, the ridge 41 may be positioned along the rod 42 such that no part of the rod 42 reaches the slotted part of the sleeve 12 to be described below, so that the sleeve 12 cannot grip the rod 42 in this orientation.

As can be seen in FIGS. 15A, 16A and 16B, a distal end of the sleeve 12 includes a slotted part including a plurality of slots 17. The slots 17 may extend at least partially along the distal end of the sleeve 12, in a direction substantially parallel to the device axis 18. FIG. 16C shows, a close up of the part of the sleeve 12 in the circle "B" shown in FIG. 16B. As can be seen in FIG. 16C, an inner surface of the slotted part of the sleeve 17 may include an inwardly facing lip 19 (facing inwardly towards the device axis 18). In the present example, the lip 19 is located at a distal end opening of the sleeve 12.

The slotted part of the sleeve 12 and the inwardly facing lip 19 can act to engage with, and grip onto, the rod 42 as it is received within the sleeve 12, forming an interference fit. This can prevent inadvertent separation of the first portion 2 and the second portion 4 during a surgical procedure, for instance as the surgeon is moving the device 10 into position for inserting the liner 30 into the cup 20. The grip provided by the lip 19 should be tight enough to prevent the first portion 2 and the second portion 4 from separating inadvertently, but should not be so tight that it interferes with the movement of the rod 42 within the sleeve 12 during insertion of the liner 30 into the cup 20.

FIGS. 15C and 15D each show an optional modification to the underside of the first portion 2 of the device 10 shown in FIGS. 11 and 12. In each of the examples shown in FIGS. 15C and 15D, the inner edges of the overhanging portions 7 of each arm 6 (namely the edge of the overhanging portion 7 which grip the surface 31 of the liner 30, and which face inward toward the device axis 18) are recessed (e.g. chamfered) at either lateral side of the arm 6. These recesses 9 may effectively reduce the contact area between the overhanging portions 7 and the surface 31 of the liner 30, and may reduce stresses within the first portion 2. As can be seen from a comparison of FIGS. 15C and 15D, the numerous different shapes and configurations for the recesses 9 themselves are envisaged.

Accordingly, there has been described a device and method for inserting a liner into an acetabular cup. The device includes a first portion configured to engage the liner and a rim of the acetabular cup to align a pole of the liner and a pole of the cup along an axis of the device prior to insertion of the liner into the cup. The device also includes a second portion for pushing the liner into the cup. The second portion includes a guide arrangement for engaging a rim of the liner. The second portion is coupled to the first portion for movement of the second portion with respect to the first portion along said axis.

Although particular embodiments of the invention have been described, it will be appreciated that many modifications/additions and/or substitutions may be made within the scope of the claimed invention.

The invention claimed is:

1. A device for inserting a liner into an acetabular cup, the device comprising:
   a first portion configured to engage the liner and a rim of the acetabular cup to align a pole of the liner and a pole of the cup along an axis of the device prior to insertion of the liner into the cup; and
   a second portion for pushing the liner into the cup, wherein the second portion comprises a guide arrangement for engaging a rim of the liner, and wherein the second portion is coupled to the first portion for movement of the second portion with respect to the first portion along said axis;
   wherein the first portion comprises a plurality of arms for engaging the liner and the rim of the acetabular cup at spaced apart points around the liner and the rim of the cup;
   wherein the guide arrangement comprises a plurality of guide members for engaging the rim of the liner at spaced apart points around the rim of the liner and wherein positions of the arms of the first portion and the guide members of the second portion are adjustable for varying a lateral distance of the arms and the guide members from said axis according to the size of the cup and the liner.

2. The device of claim 1, wherein the arms of the first portion and the guide members of the second portion extend at an acute angle with respect to said axis, and wherein the device further comprises an outer sleeve configured to adjust the positions of the arms and guide members by sliding along the device in a direction parallel to said axis to push the arms and guide members inward toward said axis.

3. The device of claim 1, wherein the first portion is configured to grip an outer surface of the liner adjacent a rim of the liner.

4. The device of claim 1 comprising a guide sleeve with a rod slidably received therein for coupling the first portion and the second portion;
   wherein an inner surface of the guide sleeve includes a lip located toward a distal end of the guide sleeve, wherein the lip extends inwardly towards said axis for forming an interference fit with the rod, for preventing inadvertent separation of the first portion and the second portion.

5. The device of claim 4, wherein the lip is located at a distal end of the sleeve, and wherein the distal end of the guide sleeve includes a plurality of slots extending substantially parallel to the device axis.

6. The device of claim 1 comprising a guide sleeve with a rod slidably received therein for coupling the first portion and the second portion;
   wherein an outer surface of the rod includes a ridge, wherein an inner surface of the guide sleeve includes a lip located at a proximal end opening of the guide sleeve, and wherein the lip and the ridge are configured to prevent inadvertent reverse mounting of the first portion and the second portion.

7. The device of claim 1, wherein the second portion comprises a button for manually pushing the second portion along said axis.

8. The device of claim 1, wherein the first portion includes one or more gripping surfaces for manually gripping the device while the liner is inserted.

9. The device of claim 1, wherein the second portion includes one or more gripping surfaces for manually gripping the device while the liner is inserted.

10. The device of claim 1, wherein the guide members are configured to push the liner into the cup as the second portion moves relative to the first portion.

11. The device of claim 1, wherein the second portion includes an engagement member for engaging an inner surface of the liner at the pole of the liner for pushing the liner into the cup as the second portion moves relative to the first portion, and wherein the guide members are arranged to engage the rim of the liner to prevent tilting of the liner relative to said axis.

12. The device of claim 11, wherein the engagement member comprises a substantially hemispherical curved outer surface for engaging with the inner surface of the liner.

13. The device of claim 1, wherein the first portion and the second portion comprise a polymer.

14. The device of claim 13, wherein the polymer comprises an acetal, a nylon, a sulfone polymer or Polyether ether ketone.

15. The device claim of claim 1, further comprising one or more non-return members configured to block movement of the second portion with respect to the first portion after the liner has been inserted into the cup, to prevent re-use of the device.

16. The device of claim 15, wherein the non-return members comprise one or more flexible arms arranged:
   in an initial position of the device, prior to insertion of the liner into the cup, urge against an outer surface of a guide sleeve of the device;
   as the second portion is moved with respect to the first portion, to slide along the outer surface of the guide sleeve; and
   to move inward toward the axis of the device when the arms reach an end of the guide sleeve, to reach a final position in which the arms block movement of the second portion with respect to the first portion, preventing the device returning to said initial position.

17. The device of claim 16, comprising a plurality of said arms located at spaced apart points around said guide sleeve.

18. The device of claim 16, comprising one or more apertures for receiving a tool to splay said flexible arms apart to receive the guide sleeve during assembly of the device.

19. The device of claim 15, comprising a guide sleeve with a rod slidably received therein for coupling the first portion and the second portion, wherein the non-return members comprise one or more collet fingers comprised in the guide sleeve, wherein the rod includes an opening for receiving the collet fingers as the liner is inserted into the cup.

20. A single use device for inserting a liner into an acetabular cup comprising:
   a first portion configured to engage the liner and a rim of the acetabular cup to align the liner and the acetabular cup with an insertion axis of the device prior to insertion of the liner into the acetabular cup;
   a second portion coupled to the first portion for pushing the liner into the acetabular cup; and
   a non-return member for preventing reuse of the device;
   wherein the device is moveable from an initial configuration to a deployed configuration; and
   wherein in the initial configuration the non-return member is configured such that the second portion may be moved with respect to the first portion along the insertion axis in a first direction to seat the liner into the acetabular cup, and in the deployed configuration the non-return member transitions to a configuration in which movement along the insertion axis in a second direction, opposite to the first direction, is prevented.

21. A device for inserting a liner into an acetabular cup, the device comprising:
a first portion configured to engage the liner and a rim of the acetabular cup to align a pole of the liner and a pole of the cup along an axis of the device prior to insertion of the liner into the cup; and
a second portion for pushing the liner into the cup, wherein the second portion comprises a guide arrangement for engaging a rim of the liner, and wherein the second portion is coupled to the first portion for movement of the second portion with respect to the first portion along said axis;
wherein the guide arrangement comprises a plurality of guide members for engaging a rim of the liner at spaced apart points around the rim;
wherein in an initial position of the device prior to insertion of the liner into the cup a gap is present between the guide members of the guide arrangement and the rim of the liner, and wherein the guide members are positioned to engage with the rim of the liner for preventing tilting of the liner as the liner is pushed into the cup;
wherein positions of arms of the first portion and the guide members of the second portion are adjustable for varying a lateral distance of the arms and the guide members from said axis according to the size of the cup and the liner.

22. A device for inserting a liner into an acetabular cup, the device comprising:
a first portion configured to engage the liner and a rim of the acetabular cup to align a pole of the liner and a pole of the cup along an axis of the device prior to insertion of the liner into the cup;
a second portion for pushing the liner into the cup, wherein the second portion comprises a guide arrangement for engaging a rim of the liner, and wherein the second portion is coupled to the first portion for movement of the second portion with respect to the first portion along said; and
a guide sleeve with a rod slidably received therein for coupling the first portion and the second portion;
wherein the first portion comprises the guide sleeve and the second portion comprises the rod.

23. A device for inserting a liner into an acetabular cup, the device comprising:
a first portion configured to engage the liner and a rim of the acetabular cup to align a pole of the liner and a pole of the cup along an axis of the device prior to insertion of the liner into the cup;
a second portion for pushing the liner into the cup, wherein the second portion comprises a guide arrangement for engaging a rim of the liner, and wherein the second portion is coupled to the first portion for movement of the second portion with respect to the first portion along said axis; and
a guide sleeve with a rod slidably received therein for coupling the first portion and the second portion;
wherein the first portion comprises the rod and the second portion comprises the guide sleeve.

24. A device for inserting a liner into an acetabular cup, the device comprising:
a first portion configured to engage the liner and a rim of the acetabular cup to align a pole of the liner and a pole of the cup along an axis of the device prior to insertion of the liner into the cup; and
a second portion for pushing the liner into the cup, wherein the second portion comprises a guide arrangement for engaging a rim of the liner, and wherein the second portion is coupled to the first portion for movement of the second portion with respect to the first portion along said axis;
wherein the second portion comprises connection means for connecting the second portion to a tool for applying a force to the second portion to push the second portion along said axis.

* * * * *